(12) United States Patent
Hotaling et al.

(10) Patent No.: US 10,709,373 B2
(45) Date of Patent: Jul. 14, 2020

(54) FLUID ANALYSIS DEVICE AND ASSOCIATED SYSTEMS AND METHODS

(71) Applicant: UNIVERSITY OF UTAH RESEARCH FOUNDATION, Salt Lake City, UT (US)

(72) Inventors: James M. Hotaling, Salt Lake City, UT (US); Randy C. Bowen, Mendon, UT (US); Alvin Y. Le, Boise, ID (US); Matthew I. Converse, Salt Lake City, UT (US); Andrew W. Southwick, Salt Lake City, UT (US); Tab S. Robbins, Layton, UT (US); Kent Ogden, Salt Lake City, UT (US); Scott McClellan, Park City, UT (US); Brian Holt, North Salt Lake, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 523 days.

(21) Appl. No.: 15/300,951

(22) PCT Filed: Mar. 30, 2015

(86) PCT No.: PCT/US2015/023364
§ 371 (c)(1),
(2) Date: Sep. 30, 2016

(87) PCT Pub. No.: WO2015/153470
PCT Pub. Date: Oct. 8, 2015

(65) Prior Publication Data
US 2017/0020433 A1    Jan. 26, 2017

Related U.S. Application Data

(60) Provisional application No. 61/995,027, filed on Mar. 31, 2014.

(51) Int. Cl.
*A61B 5/20* (2006.01)
*B01L 3/00* (2006.01)
(Continued)

(52) U.S. Cl.
CPC .......... *A61B 5/208* (2013.01); *A61B 5/14507* (2013.01); *A61B 10/007* (2013.01);
(Continued)

(58) Field of Classification Search
CPC ... A61B 5/208; A61B 5/14507; A61B 5/0002; A61B 10/007; B01L 3/502; G01F 1/56; G01N 27/221; G01N 27/493
See application file for complete search history.

(56) References Cited

U.S. PATENT DOCUMENTS 4,051,431 A    9/1977 Wurster
4,343,316 A    8/1982 Jespersen
(Continued)

FOREIGN PATENT DOCUMENTS

ES    2439422    1/2014
WO    WO 99/10714    3/1999
(Continued)

OTHER PUBLICATIONS

Otero et al., "A New Device to Automate the Monitoring of Critical Patients' Urine Output," Hindawi Publishing Corporation, 2014, Article ID 587593, pp. 1-8.
(Continued)

*Primary Examiner* — Robert J Eom
(74) *Attorney, Agent, or Firm* — Fogg & Powers LLC

(57) ABSTRACT

A fluid analysis device including a fluid receipt chamber, a first capacitive element for measuring fluid flow into the fluid receipt chamber and a controller operatively coupled to
(Continued)

the first capacitive element, wherein the controller is configured to measure a first capacitance of the first capacitive element.

40 Claims, 16 Drawing Sheets

(51) Int. Cl.
| | |
|---|---|
| *G01F 1/56* | (2006.01) |
| *G01N 27/22* | (2006.01) |
| *G01N 33/493* | (2006.01) |
| *A61B 10/00* | (2006.01) |
| *A61B 5/145* | (2006.01) |
| *A61B 5/00* | (2006.01) |

(52) U.S. Cl.
CPC ............... *B01L 3/502* (2013.01); *G01F 1/56* (2013.01); *G01N 27/221* (2013.01); *G01N 33/493* (2013.01); *A61B 5/0002* (2013.01); *A61B 2560/0223* (2013.01); *A61B 2560/0238* (2013.01); *A61B 2560/0431* (2013.01); *A61B 2562/0214* (2013.01); *B01L 2200/0605* (2013.01); *B01L 2200/143* (2013.01); *B01L 2200/148* (2013.01); *B01L 2300/0627* (2013.01); *B01L 2300/0832* (2013.01); *B01L 2300/0848* (2013.01)

(56) References Cited

U.S. PATENT DOCUMENTS

| | | | |
|---|---|---|---|
| 4,394,502 | A | 7/1983 | Maruyama |
| 4,397,189 | A | 8/1983 | Johnson et al. |
| 4,417,473 | A | 11/1983 | Tward et al. |
| 4,554,687 | A | 11/1985 | Carter et al. |
| 4,589,077 | A | 5/1986 | Pope |
| 4,589,280 | A | 5/1986 | Carter |
| 4,628,612 | A | 12/1986 | Hori et al. |
| 4,683,748 | A | 8/1987 | Carter |
| 4,730,499 | A | 3/1988 | Gianella et al. |
| 4,891,993 | A | 1/1990 | Barker |
| 5,046,510 | A | 9/1991 | Ams et al. |
| 5,062,304 | A | 11/1991 | Van Buskirk et al. |
| 5,122,272 | A | 6/1992 | Iana et al. |
| 5,423,214 | A | 6/1995 | Lee |
| 5,726,908 | A | 3/1998 | Hosmer et al. |
| 5,769,087 | A | 6/1998 | Westphal et al. |
| 6,138,508 | A | 10/2000 | Hannan et al. |
| 6,490,920 | B1 | 12/2002 | Netzer |
| 7,188,426 | B2 | 3/2007 | Barr |
| 7,360,424 | B2 | 4/2008 | Urano et al. |
| 7,611,500 | B1 | 11/2009 | Lina et al. |
| 7,638,340 | B2 | 12/2009 | Tanaka et al. |
| 7,722,584 | B2 | 5/2010 | Tanaka et al. |
| 7,845,224 | B2 | 12/2010 | Barlesi et al. |
| 8,116,993 | B2 | 2/2012 | Cebulski |
| 8,276,465 | B2 | 10/2012 | Belotserkovsky |
| 8,337,476 | B2 | 12/2012 | Greenwald et al. |
| 8,549,764 | B2 | 10/2013 | Muyskens et al. |
| 8,590,375 | B2 * | 11/2013 | Farmanyan ............ G01F 23/268 324/668 |
| 2005/0092606 | A1 | 5/2005 | Reich et al. |
| 2005/0282265 | A1 * | 12/2005 | Vozza-Brown ........ C12M 23/08 435/285.2 |
| 2008/0060422 | A1 * | 3/2008 | Hosoya ................ A61B 10/007 73/53.01 |
| 2009/0010804 | A1 * | 1/2009 | Withrow, III ........ A61B 5/0002 422/68.1 |
| 2011/0000309 | A1 | 1/2011 | Griffiths et al. |
| 2011/0083504 | A1 | 4/2011 | Unger |
| 2013/0030262 | A1 | 1/2013 | Burnett et al. |

FOREIGN PATENT DOCUMENTS

| | | |
|---|---|---|
| WO | WO 2013/128376 | 9/2013 |
| WO | WO 2014/141234 | 9/2014 |
| WO | WO 2014/145971 | 9/2014 |
| WO | WO 2015/153470 | 10/2015 |

OTHER PUBLICATIONS

RussianPatents.com, "Capacitance fluid amount sensor for urofluometer," <http://russianpatents.com/patent/225/2256884.html> published 2013, 2 pages.
Chiang et al., "A Semicylindrical Capacitive Sensor With Interface Circuit Used for Flow Rate Measurement," IEEE Sensors Journal, vol. 6, No. 6, Dec. 2006, pp. 1564-1570.
International Search Report and Written Opinion for Application No. PCT/US2015/023364 dated Jul. 6, 2015 (15 pages).
Mehta et al., "Comparative evaluation of the diagnostic significance of circulating immune complexes and antibodies to phosphatidylinositomannosides in pulmonary tuberculosis by enzyme-linked immunosorbent assay," Med Microbiol Immunol (1989) 178:229-233.
van Pittius et al., "The ESAT-6 gene cluster of Mycobacterium tuberculosis and other high G+C Gram-positive bacteria," Genome Biology 2001, pp. 1-18.
Doskeland et al., "Bacterial antigen detection in body fluids: method for rapaid antigen concentration and reduction of nonspecific reactions," J. Clin. Microbiol. 1980, 11(4):380-384.
Bhattacharya et al., "Antibody-Based Enzyme-Linked Immunosorbent Assay for Determination of Immune Complexes in Clinical Tuberculosis," AM REV RESPIR DIS 1986; 134:205-209.
Trent et al., "Diversity of endotoxin and its impact on pathogenesis," Journal of Endotoxin Research 2006 12: 205-223.
Lodowska et al., "The sugar 3-deoxy-D-manno-oct-2-ulosonic acid (Kdo) as a characteristic component of bacterial endotoxin—a review of its biosynthesis, function, and placement in the lipopolysaccharide core," Can. J. Microbiol. 59: 645-655 (2013).
Guérardel et al., "Structural Study of Lipomannan and Lipoarabinomannan from Mycobacterium chelonae," The Journal of Biological Chemistry, vol. 277, No. 34, Issue of Aug. 23, pp. 30635-30648, 2002.
Anderson et al. "Factors affecting the Amount and Composition of the Serum Seromucoid Fraction," Nature, vol. 208, Oct. 30, 1965, pp. 491-492.
Radhakrishnan et al., "Diagnostic significance of circulating immune complexes in patients with pulmonary tuberculosis," J. Med. Microbiol.—vol. 36 (1992), 128-131.
Ingham et al., "Precipitation of Proteins with Polyethylene Glycol," Methods in Enzymology, vol. 182, 1999, 301-306.
Chatterjee et al., "The mycobacterial cell wall: structure, biosynthesis and sites of drug action," Current Opinion in Chemical Biology 1997, 1 :579-588.
Mishra et al., "Lipoarabinomannan and related glycoconjugates: structure, biogenesis and role in Mycobacterium tuberculosis physiology and host-pathogen interaction," FEMS Microbiol Rev 35 (2011) 1126-1157.
Trøseid et al., "Circulating levels of HMGB1 are correlated strongly with MD2 in HIV-infection: Possible implication for TLR4-signalling and chronic immune activation," Innate Immunity 19(3), 2012, 290-297.
Fukuda et al., "Critical Roles for Lipomannan and Lipoarabinomannan in Cell Wall Integrity of Mycobacteria and Pathogenesis of Tuberculosis," 2013, mBio 4(1):e00472-12. doi:10.1128/mBio.00472-12, 1-11.
Petsch et al., "Proteinase K Digestion of Proteins Improves Detection of Bacterial Endotoxins by the Limulus Amebocyte Lysate Assay: Application for Endotoxin Removal from Cationic Proteins," Analytical Biochemistry 259, 42-47 (1998).
Krzyzowska et al., "Lipoambinomannan as a Regulator of the Monocyte Apoptotic Response to Mycobacterium bovis BCG Danish Strain 1331 Infection ," Polish Journal of Microbiology 2007, vol. 56, No. 2, 89-96.

(56) References Cited

OTHER PUBLICATIONS

Inada et al., "Establishment of a New Perchloric Acid Treatment Method to Allow Determination of the Total Endotoxin Content in Human Plasma by the Limulus Test and Clinical Application," Microbial. Immunol. vol. 35 (4), 303-314, 1991.
Raja et al., "Characterization of mycobacterial antigens and antibodies in circulating immune complexes from pulmonary tuberculosis," J Lab Clin Med, vol. 125, No. 5, May 1995, 581-587.
Samuel et al., "Significance of circulating immune complexes in pulmonary tuberculosis," Clin. exp. Immunol. (1984) 58, 317-324.
Suda et al., "Application of a new perchloric acid treatment method to measure endotoxin in both amniotic fluid and cord blood by an endotoxinspecific chromogenic Limulus test in intra-amniotic infection," Acta Paediatrica Japonica (1996) 38, 444-448.
Karima et al., "The molecular pathogenesis of endotoxic shock and organ failure," Molecular Medicine Today, Mar. 1999, 123-132.
Rietschel et al., "Bacterial endotoxin: molecular relationships of structure to activity and function," The FASEB Journal, vol. 8, Feb. 1994, 217-225.
Petsch et al., "Endotoxin removal from protein solutions," Journal of Biotechnology 76 (2000) 97-119.
Obayashi et al., "Endotoxin-Inactivating Activity in Normal and Pathological Human Blood Samples," Infection and Immunity, Aug. 1986, p. 294-297.
Carr et al., "Immune complexes and antibodies to BCG in sera from patients with mycobacterial infections," Clin. exp. Immunol. (1980) 39, 562-569.
Mennink-Kersten et al., "Detection of circulating galactomannan for the diagnosis and management of invasive aspergillosis," The LANCET Infectious Diseases vol. 4 Jun. 2004, 349-357.
Beutler et al., "Innate immune sensing and its roots: the story of endotoxin," Nature Reviews | Immunology, vol. 3, Feb. 2003, 169-176.
Wood et al., "Challenges facing LAM urine antigen tests for diagnosing HIV-associated tuberculosis," Expert Rev Mol Diagn. Jul. 2012; 12(6): 549-551.
Trøseid et al., "Elevated plasma levels of lipopolysaccharide and high mobility group box-1 protein are associated with high viral load in HIV-1 infection: reduction by 2-year antiretroviral therapy," AIDS 2010, 24:1733-1737.
Briken et al., "Mycobacterial lipoarabinomannan and related lipoglycans: from biogenesis to modulation of the immune response," Molecular Microbiology (2004) 53(2), 391-403.
Chatterjee et al., "Mycobacterial lipoarabinomannan: an extraordinary lipoheteroglycan with profound physiological effects," Glycobiology vol. 8 No. 2 pp. 113-120, 1998.
Feruglio et al., "Soluble Markers of the Toll-Like Receptor 4 Pathway Differentiate between Active and Latent Tuberculosis and Are Associated with Treatment Responses," PLoS ONE 8(7): e69896, Jul. 2013, 1-8.
Bhat et al., "Steric exclusion is the principal source of the preferential hydration of proteins in the presence of polyethylene glycols," Protein Science (1992), 1, 1133-1143.
Atha et al., "Mechanism of Precipitation of Proteins by Polyethylene Glycols, Analysis in Terms of Excluded Volume," The Journal of Biological Chemistry, vol. 256, No. 23. Issue of Dec. 10, 1981, 12108-12117.
Sharma et al., "Endotoxin Detection and Elimination in Biotechnology," Biotechnology and Applied Biochemistry 8, 5-22 (1986).
Udaykumar et al., "Analysis of circulating immune complexes (CIC) in tuberculosis: levels of specific antibody and antigens in CIC and relationship with serum antibody," FEMS Microbiology Immunology 76 (1991) 135-142.
Hurley et al., "Endotoxemia: Methods of Detection and Clinical Correlates," Clinical Microbiology Reviews, Apr. 1995, p. 268-292.
Barnes et al., "Cytokine Production Induced by Mycobacterium tuberculosis Lipoarabinomannan," The Journal of Immunology, vol. 149. 541-547. No. 2, Jul. 15, 1992.
Ellwood, "The Distribution of 2-Keto-3-deoxy-octonic Acid in Bacterial Walls," J. gen. Microbiol. (1970), 60, 373-380.
Obayashi et al., "Addition of perchloric acid to blood samples for colorimetric limulus test using chromogenic substrate: Comparison with conventional procedures and clinical applications," The Journal of laboratory and clinical medicine, vol. 104, Issue 3, 1984, 321-330.
Gillespie et al., "Detection of C-polysaccharide in serum of patients with *Streptococcus pneumoniae* bacteraemia,".
Sada et al., "Detection of lipoarabinomannan as a diagnostic test for tuberculosis," J. Clin. Microbiol. 1992, 30(9):2415-2418.
Elass et al., "Identification by surface plasmon resonance of the mycobacterial lipomannan and lipoarabinomannan domains involved in binding to CD14 and LPS-binding protein," FEBS Letters 581 (2007) 1383-1390.
Raja et al., "Immunoglobulin G, A, and M Responses in Serum and Circulating Immune Complexes Elicited by the 16-Kilodalton Antigen of Mycobacterium tuberculosis," Clin. Diagn. Lab. Immunol. 2002, 9(2):308-312.
Sakamuri et al., "Association of Lipoarabinomannan with Human High Density Lipoprotein in Blood: Implications for Biodistribution and Serum Diagnostics," Tuberculosis (Edinb). May 2013; 93 (3): 1-13.
De Jonge et al., "A simple and rapid treatment (trichloroacetic acid precipitation) of serum samples to prevent non-specific reactions in the immunoassay of a proteoglycan," Journal of immunological methods, vol. 99, Issue 2, 1987, 195-197.
European Patent Office Extended Search Report for Application No. 15772898.1 dated Nov. 14, 2017 (14 pages).

* cited by examiner

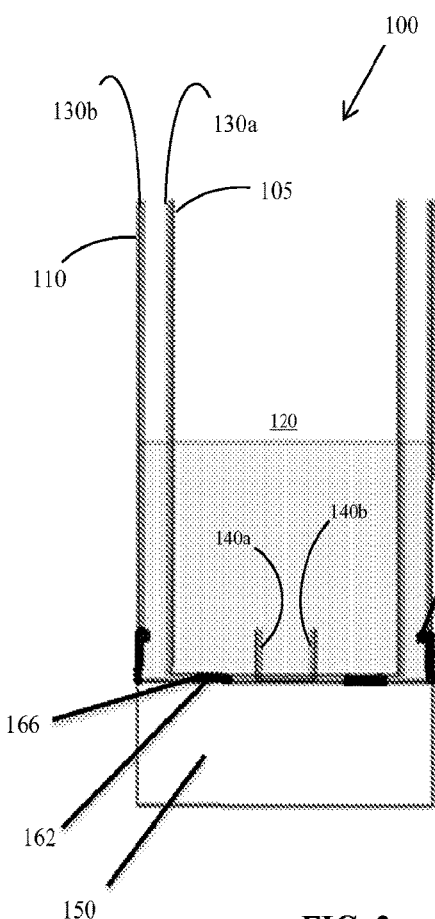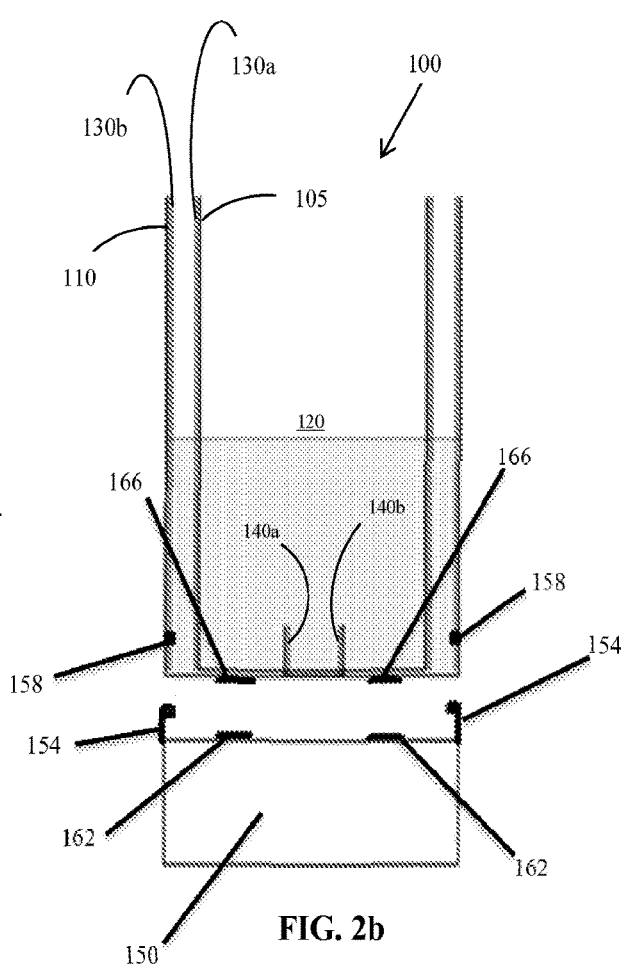
FIG. 2a
FIG. 2b
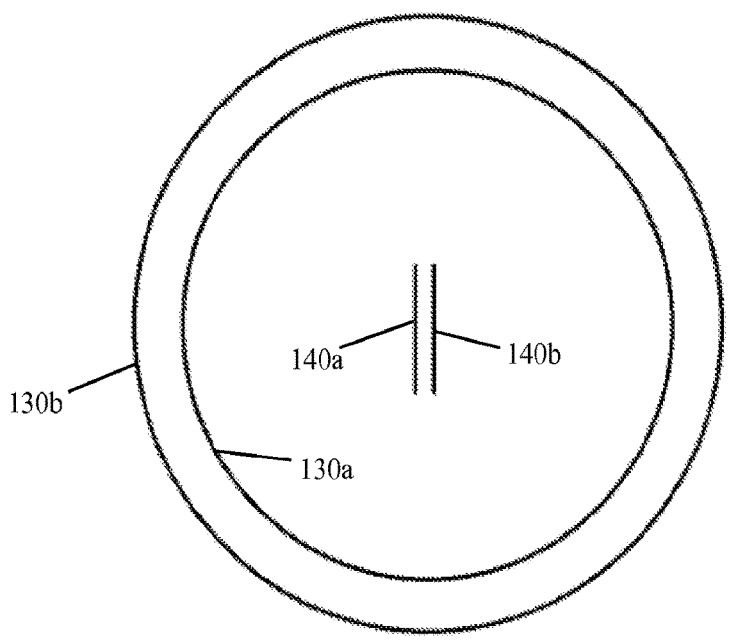
FIG. 2c

FLUID ANALYSIS DEVICE AND ASSOCIATED SYSTEMS AND METHODS

CROSS-REFERENCE TO RELATED APPLICATIONS

This is a U.S. national stage entry of International Patent Application No. PCT/US2015/023364, filed on Mar. 30, 2015, which claims priority to U.S. Provisional Patent Application No. 61/995,027, filed on Mar. 31, 2014, the entire contents of all of which are fully incorporated herein by reference.

BACKGROUND

The present invention relates to a device for measuring fluid and fluid flow characteristics.

Uroflowmetry can measure the volume of urine released from the body, the rate at which urine is voided, and the time it takes to complete a voiding event. The results of a uroflowmetry test can be very beneficial in evaluating the health of the urinary tract. This test can also be very valuable in diagnosing abnormal health conditions, such as lower urinary tract symptoms, benign prostatic hypertrophy, prostate cancer, bladder tumor, neurogenic bladder dysfunction, urinary incontinence, urinary blockage, urinary tract infection, as well as other conditions. Traditionally, uroflowmetry tests are conducted at a medical facility, such as a hospital or clinic. Testing in an artificial clinical setting opposed to a natural setting such as the patient's home can have a significant impact on the patient's performance. In addition to the obvious disadvantages of inconvenience and patient compliance, one complication that often arises with in-clinic testing is that the patient will need to urinate while waiting for the test to be administered. This can result in premature voiding or abnormal voiding events, which skew or negate the value of the test and require the patient to return to the clinic multiple times to get accurate results.

SUMMARY

In one embodiment, the invention provides a fluid analysis device including a fluid receipt chamber, a first capacitive element for measuring fluid flow into the fluid receipt chamber and a controller operatively coupled to the first capacitive element, wherein the controller is configured to measure a first capacitance of the first capacitive element.

Other aspects of the invention will become apparent by consideration of the detailed description and accompanying drawings.

BRIEF DESCRIPTION OF THE DRAWINGS

FIGS. 2a and 2b are cross-sectional views of a second embodiment of a fluid analysis device with a detachable base secured to the device (FIG. 2a) and with the detachable base removed from the device (FIG. 2b).

FIG. 2c is a top view of the second embodiment of the fluid analysis device.

DETAILED DESCRIPTION

Figure 1:
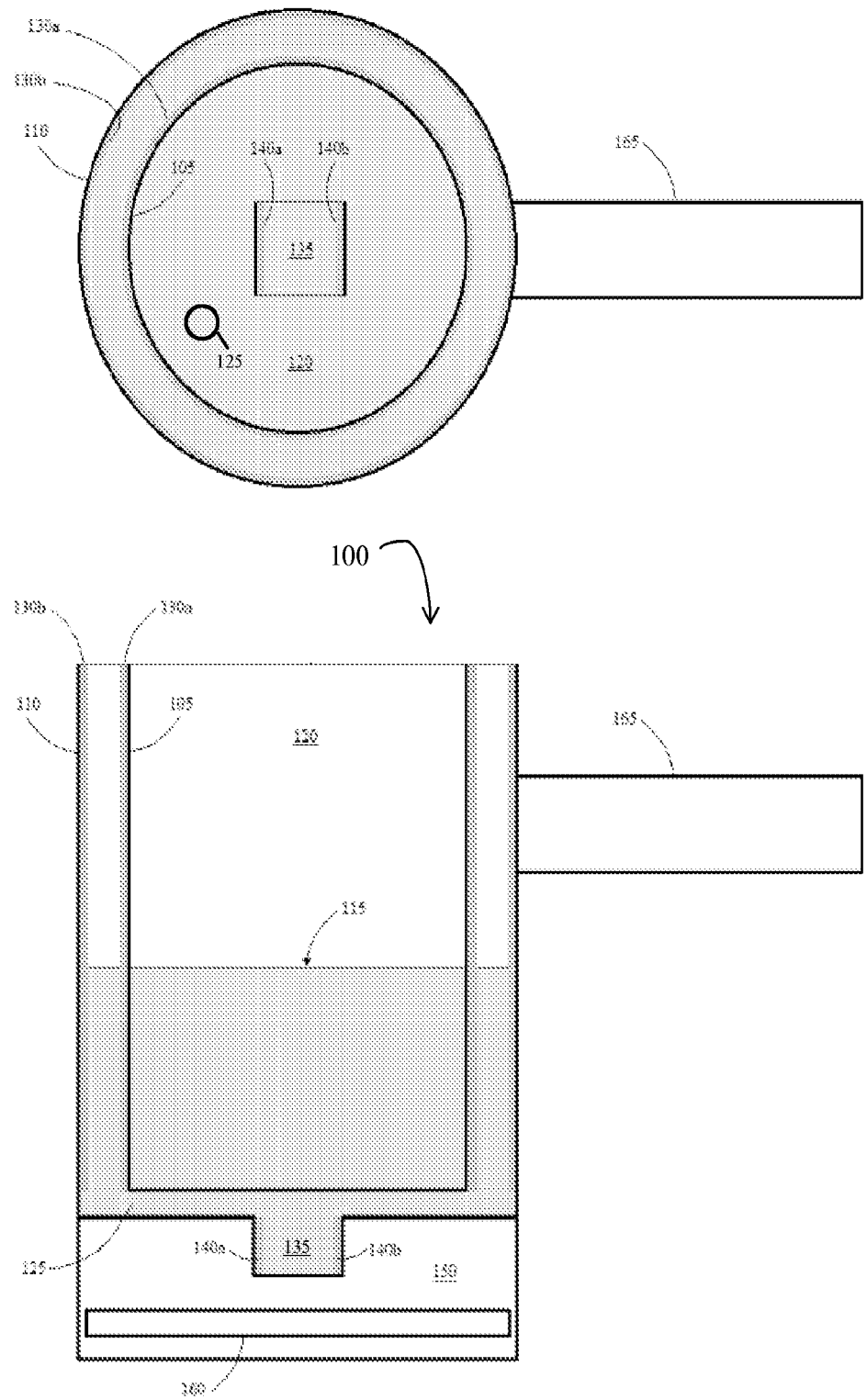
FIG. 1 is a cross-sectional view of an embodiment of a fluid flow measuring device.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used herein, the singular forms "a," "an" and "the" include plural referents unless the context clearly dictates otherwise. Thus, for example, reference to "a sensor" includes a plurality of such sensors.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical (i.e. physical) manner Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, a "subject" refers to an animal. In one aspect the animal may be a mammal. In another aspect, the mammal may be a human.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Reference in this specification may be made to devices, structures, systems, or methods that provide "improved" performance. It is to be understood that unless otherwise stated, such "improvement" is a measure of a benefit obtained based on a comparison to devices, structures, systems or methods in the prior art. Furthermore, it is to be understood that the degree of improved performance may vary between disclosed embodiments and that no equality or consistency in the amount, degree, or realization of improved performance is to be assumed as universally applicable.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., instructions stored on non-transitory computer-readable medium) executable by one or more processing units, such as a microprocessor and/or application specific integrated circuits ("ASICs"). As such, it should be noted that a plurality of hardware and software based devices, as well as a plurality of different structural components may be utilized to implement the invention. For example, "servers" and "computing devices" described in the specification can include one or more processing units, one or more computer-readable medium modules, one or more input/output interfaces, and various connections (e.g., a system bus) connecting the components.

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Uroflowmetry is a test used to measure one or more of the volume of urine released from the body, the rate at which urine is voided, and the time it takes to complete a voiding event. Not only can uroflowmetry be very useful in evaluating the health of the urinary tract, it can also be very valuable in diagnosing a variety of abnormal health conditions. These conditions can include lower urinary tract symptoms (LUTS), benign prostatic hypertrophy, prostate cancer, bladder tumor, neurogenic bladder dysfunction, urinary incontinence, urinary blockage, urinary tract infection, as well as other conditions.

In one specific example, uroflowmetry can be valuable in evaluating LUTS. LUTS refers to a clinical presentation in men with symptoms such urinary hesitance, post-void dribbling, urgency, and nocturia. Traditionally, LUTS in men has been attributed to benign prostatic enlargement and consequent bladder outlet obstruction. Patients who present with symptoms of LUTS undergo a physical and medical history examination typically performed by a primary care physician. A referral to a specialist involves a diagnostic evaluation prior to initiating treatment or invasive therapies. It is currently estimated that 198 in every 100,000 male visits to the emergency room (ER) are due to LUTS. Approximately 9.5% of these ER visits result in hospitalization. Furthermore, approximately 44.6% of these cases result in catheterization, of which 17.4% result in infection.

Assessment of LUTS can involve urine flow rate measurement, post-void residual determination (PVR) (which uses ultrasound), and cystoscopy. Urinary flow rate is standardized and well accepted as a criterion for assessment of flow patterns in screening for Bladder Outlet Obstruction conditions. However, clinic-based uroflowmetry can be flawed because the setting is artificial and often it can be difficult for the patient to void at the desired moment. Additionally, a single measurement of the voided parameters can be a poor representation of the patient's condition due to the high variability (25%) of the measured parameters. Hence, in clinical practice, multiple uroflowmetry measurements and many visits to the clinic can be necessary for accurate results.

Embodiments set forth herein provide fluid analysis devices and related systems and methods that can facilitate a more natural (and therefore accurate) collection of uroflowmetry data. Such a device can have a number of basic components including without limitation, a fluid receipt chamber, a first capacitive element, a second capacitive element, a tilt sensor (e.g. accelerometer or inclinometer), and associated circuitry. Each of these components is discussed in further detail below.

Referring to FIG. 1, a cross-sectional view of one embodiment of an exemplary fluid analysis device is illustrated. The device is depicted generally as 100. The device 100 can have a base 150 supporting a fluid receipt chamber 120 with an inner cylinder or inner wall 105 and a cup-shaped outer wall 110 having at least one handle 165 formed integrally with the outer wall 110 or detachably coupled thereto. The outer wall 110 may also include a spout or groove. An inner fluid receipt chamber 120 is adapted to receive any suitable fluid 115 for measuring fluid and fluid flow characteristics. In one embodiment, the fluid 115 is urine. However, other fluids with biomedical applications (e.g., blood, amniotic fluid, etc.) may also be used, as well as many other organic and inorganic fluids (silicones, oils, cleaning agents, chemicals, water, etc.). In various embodiments, additional sensors may be included in the device to provide additional data regarding properties of the fluid (e.g. temperature, pH, density, and presence of ketones, among other properties), as discussed further below. The inner cylinder 105 defines an inner fluid compartment, which is part of the fluid receipt chamber 120, having at least one passage 125 for allowing the fluid 115 to pass between the inner fluid compartment of the inner cylinder 105 and the outer wall 110, the wall of the outer wall 110 can define the outer wall of the fluid analysis device 100. More particularly, fluid passes between the inner fluid compartment of the inner cylinder 105 and the fluid space between the inner cylinder 105 and the outer wall 110 via the passage 125. The passage 125 may be a single channel around a lower end of the inner cylinder, or multiple passages 125 may exist. In some embodiments, the passages are a plurality of holes in the inner cylinder. These holes may be spaced symmetrically or randomly, and may be of the same general size and shape or of varying sizes and shapes. In various embodiments, the inner wall 105 and/or the outer wall 110 of the fluid receipt chamber may be rigid or flexible.

With continued reference to FIG. 1, the device 100 includes a first capacitive element (in certain embodiments referred to as a cup capacitor) having an inner capacitive plate 130a and an outer capacitive plate 130b to measure fluid and flow characteristics of the fluid 115. Appropriate circuitry and other operative elements, such as a power source, tilt sensor (e.g. accelerometer or inclinometer), communication module, controller, and the like can be included in the base 150 as part of an electronics unit 160. In the illustrated construction, the inner capacitive plate 130a is disposed about an outer periphery of the inner cylinder 105, and the outer capacitive plate 130b is disposed about the inner surface of the outer wall 110 defining a region therebetween. The device 100 also includes a second capacitive element or normalization capacitor, having two capacitive plates 140a and 140b, used to normalize data collected by the first capacitive element. In various embodiments, the plates 130a, 130b of the first capacitive element have an area of between 100-1000 $cm^2$ and the plates 140a, 140b of the second capacitive element have an area of between 1-30 $cm^2$, although other plate sizes are possible for either of the first and second capacitive elements. In various embodiments, each of the pairs of plates 130a, 130b and 140a, 140b has a spacing therebetween in a range of 3 mm to 35 mm. However, this spacing may be varied depending on the viscosity of the fluid, for example the spacing may be larger if a more viscous fluid is being analyzed. As shown in FIG.

1, the second capacitive element may be disposed within a recess 135 on a bottom surface inside the space defined by the outer wall 110, ensuring the second capacitive element is filled completely with the fluid. In certain embodiments the recess 135 has a volume of between 1-20 mL and the device has a maximum capacity of between 100 mL-1000 mL. In the illustrated construction, the plates 140a, 140b are rectangular sections disposed on sidewalls of a rectangular recess 135. However, the location and shape of the recess 135 and plates 140a, 140b are exemplary by nature and may be varied in any suitable manner. Furthermore, in some embodiments the second capacitive element may not be disposed within a recess, but rather may be placed in any location in the device 100 such the second capacitive element fills completely in response to fluid being added, for example on or near the bottom surface of the fluid receipt chamber 120 (see FIGS. 2a, 2b, 2c).

Figure 3:
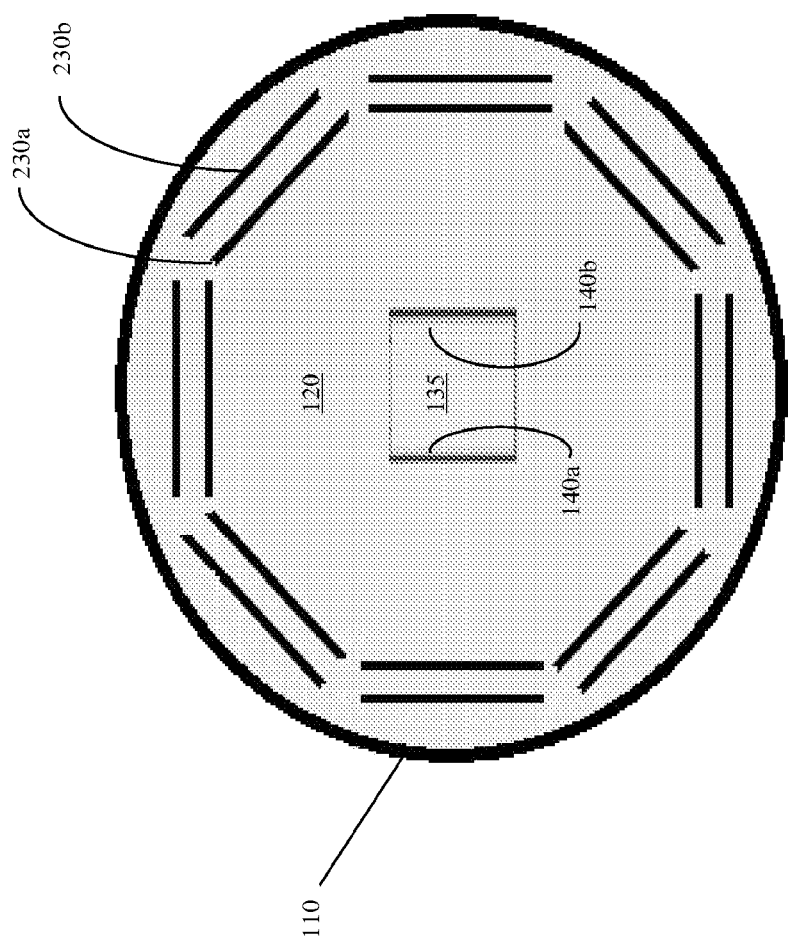
FIG. 3 is a top view of a third embodiment of the fluid analysis device.

Furthermore, in various embodiments, such as the embodiment illustrated in FIG. 3, the first capacitive element may be made of two or more pairs of plates 230a, 230b instead of a single (e.g. cylinder-shaped) pair of plates. In this latter case, the multiple pairs of plates 230a, 230b may be pairs of vertically-oriented (e.g. oriented from top to bottom of the fluid receipt chamber 120) plates adjacent to one another with a gap in between into which fluid flows. These pairs of plates are generally arranged in a symmetrical pattern around the perimeter of the fluid receipt chamber 120 to promote tilt-independence of capacitance measurements, as discussed further below.

In operation, the fluid 115 enters the fluid receipt chamber 120, flows through at least one passage 125, and enters the space defined by the outer wall 110, filling the outer wall 110 (including the fluid space between the outer wall 110 and the inner wall 105) to the same level as the inner fluid compartment of the inner fluid receipt chamber 120. As the fluid level rises within the outer wall 110, it passes between the first capacitive element having the inner capacitive plate 130a and the outer capacitive plate 130b. The first capacitive element measures the fluid flow characteristics of the fluid 115. The second capacitive element, having two capacitive plates 140a and 140b, is filled completely and is used to normalize the data collected by the first capacitive element. In general, the second capacitive element will be determined to be completely covered or filled with fluid when an associated signal of the second capacitive element has plateaued (e.g., ceases to change meaningfully). In contrast, the first capacitive element will generally continue to change as fluid is added.

In another embodiment, shown in FIGS. 2a-2c, the base 150 containing appropriate circuitry and other operative elements may be detachable from the remainder of the device 100, which houses the first and second capacitive elements. The base 150 may be a cylindrical, or 'puck'-shaped, container forming a housing for the electronics unit 160 including the circuitry and other operative elements. The base 150 is configured to be mechanically and electrically coupled to the device 100 in any suitable manner. For example, the base 150 may include engagement features 154 to mechanically secure the base 150 to the corresponding features 158 on the device 100 by known methods (e.g., press fitting, threaded engagement, slide-on features, snap-on features, etc.). The base 150 further includes some form of electrical contacts, which may be formed separately from or integrally with the engagement features, to electrically couple the base 150 to the device 100. In the embodiment illustrated in FIGS. 2a-2c, the base 150 includes multiple electrical contacts 162 on the top of the base 150 that engage electrical contacts 166 located on a bottom surface of the device 100. The engagement features 154, 158 may also help to form a seal to protect the electrical contacts 162, 166 (e.g., from the fluid).

Figure 4A:
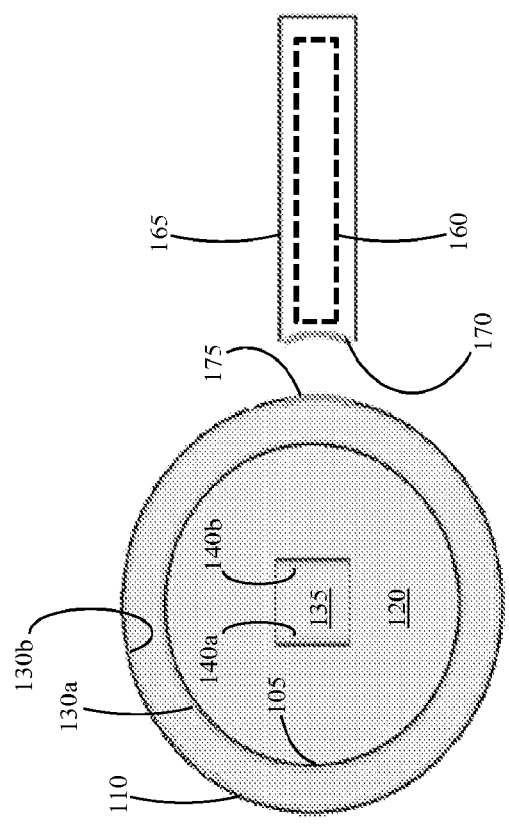
FIG. 4a is a top view a fourth embodiment of the fluid analysis device, illustrating a detachable handle attached to the device (left) and detached from the device (right).
Figure 4A:
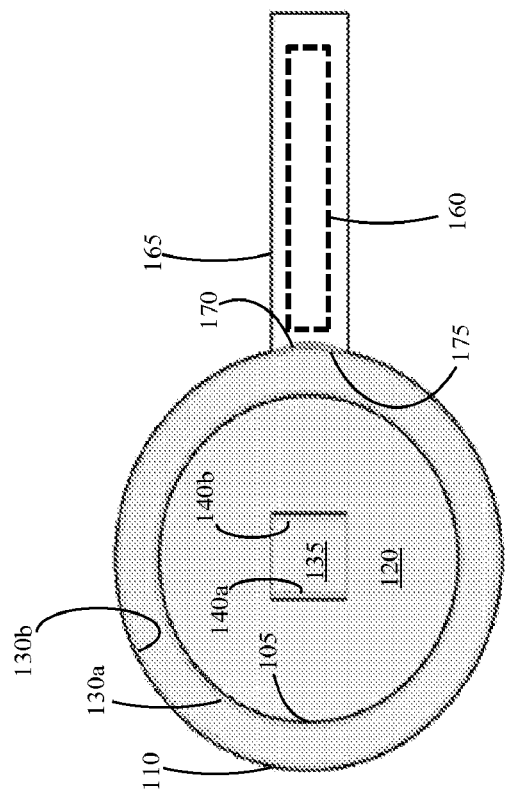
Figure 4B:
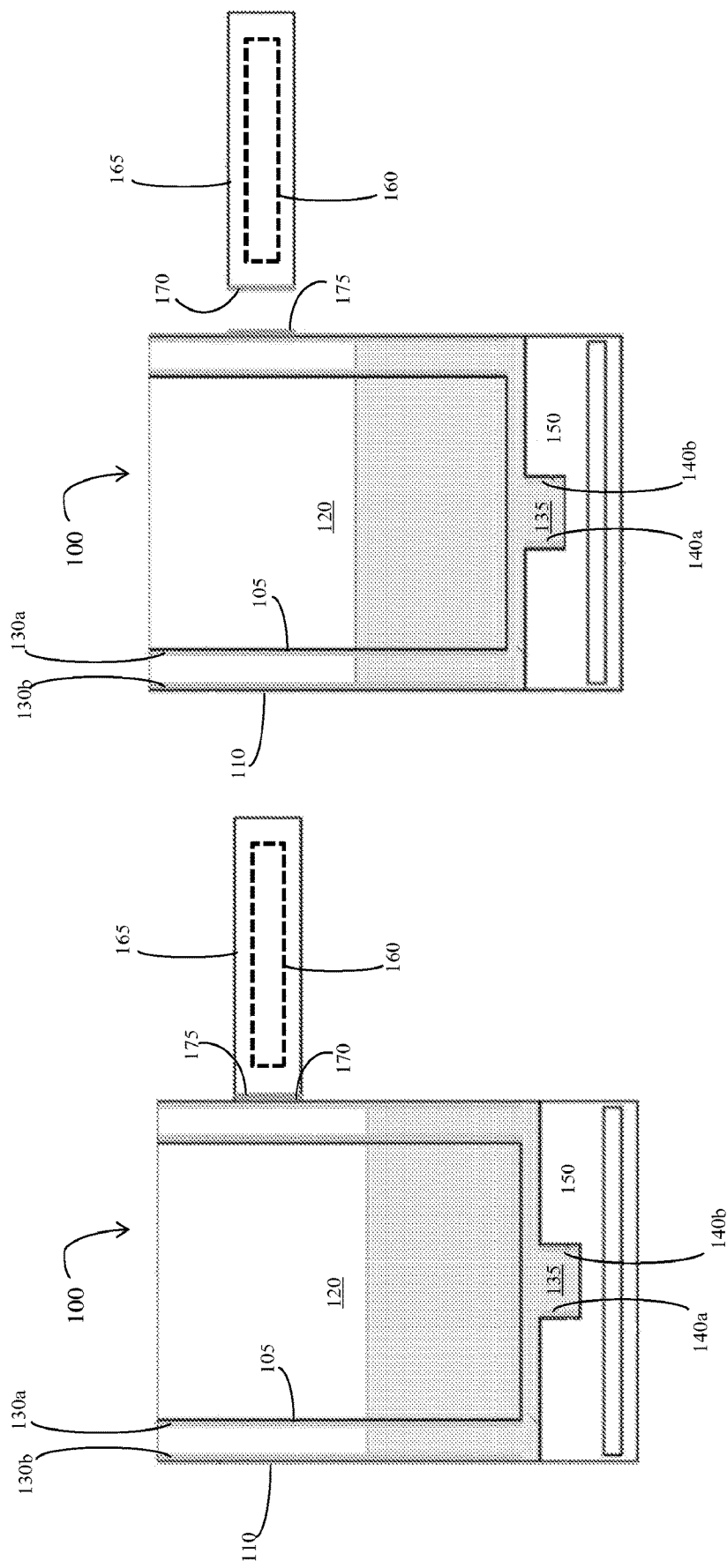
FIG. 4b is a cross-sectional view of the device shown in FIG. 4a, illustrating the detachable handle attached to the device (left) and detached from the device (right).

In the embodiment illustrated in FIGS. 4a and 4b, the electronics unit 160 including the circuitry and other operative elements may be placed in a detachable handle 165 of the device 100. The handle 165 in such embodiments includes multiple electrical contacts 170 on a side of the handle 165 that are configured to form an electrical connection with corresponding contacts 175 disposed on the outer wall 110 of the device 100 to allow for electrical communication with the first and second capacitive elements. In this embodiment, the electrical contacts 175 of the device 100 are disposed at the location at which the handle 165 engages the device 100 (e.g., along the outer wall 110). In addition, the handle 165 may be mechanically secured to the outer wall 110 by a number of known methods (e.g., press fitting, threaded engagement, slide-on features, snap features, etc.). The method of securing the handle 165 to the device 100 ensures that there is a sealed electrical connection between the electrical contacts 170, 175 and that at most only a limited amount of stress is placed on the electrical connections 170, 175 when the device 100 is supported solely by the handle 165.

Though FIGS. 1 and 2a-2c show an embodiment with two concentric cylindrical walls, more than two concentric walls can be used for added redundancy. In other embodiments, the device 100 can have other multiple chamber configurations beside the 'cylinder within a cylinder' design as described above, such as side by side chambers which allow the inclusion of multiple capacitive elements having separate plates between which fluid can enter for the purposes of making a capacitive measure of fluid flow. In a further embodiment, the device 100 can have a first inner fluid receipt chamber for receiving fluid and an outer chamber or reservoir fluidly coupled or connected thereto. In use, fluid is admitted into either the inner or the outer chamber and then proceeds into the other chamber and properly located first and second capacitive elements receive the fluid and measure the flow thereof in a normalized manner as a function of change in capacitance. Nearly any configuration that allows the accurate measure of fluid flow can be used.

As described above, the inner fluid compartment of the inner wall 105 can be adapted to receive fluid into the device 100. The inner wall 105 or reservoir may include a single passage 125 leading to the outer cup 110 or space between the inner wall 105 and outer wall 110, or the device 100 can include a plurality of passages 125. In general, the total area of the passage or passages 125 should be sufficient to allow for the fluid 115 to enter the fluid space between the inner wall 105 and the outer wall 110 at a rate equivalent to the rate at which fluid is dispensed into the device (e.g. in a range of 10-15 mL/sec) in order to achieve an accurate fluid flow measurement. In certain embodiments, the area of the passage or passages 125 may be limited in order to reduce spurious changes in capacitance which could arise due to sudden movements of the device 100; without any limits being placed on the flow of fluid 115 through the passage(s) 125, levels of fluid 115 in the fluid space between the inner wall 105 and the outer wall 110 could rapidly increase and decrease if the device 100 were moved suddenly. In various embodiments, the total area of the passage(s) is between 0.1-1,000 mm$^2$, and in certain embodiments the total area is between 500-800 mm$^2$. However, in other embodiments where a more viscous fluid is being analyzed, the area may be substantially larger to allow proper flow of the fluid through the passage. Given that the device 100 in some embodiments is intended to be used as a portable device for in-office or at-home use, the dampening or restriction of spurious fluid movements is expected to provide more stable and accurate capacitance measurements. In other embodiments, the fluid space between the inner wall 105 and the outer wall 110, in conjunction with the total area of the passages(s), provides a mechanical dampening of the incoming fluid (e.g. due to factors including surface tension of the fluid), which helps reduce potential fluid measurement artifacts caused by sudden movement of the device 100.

In one aspect, the device 100 can be adapted to be disposable. Disposable elements may include the inner cylinder 105 with attached inner capacitive plate 130a, the outer capacitive plate 130b, and/or the entire fluid receipt chamber 120 including all of the capacitive elements 130a, 130b, 140a, 140b. The device 100 may also be adapted to be reusable, handheld, and cleanable. Furthermore, the device 100 may be adapted to include replaceable walls or wall covers that can facilitate cleaning of the device.

Figure 5:
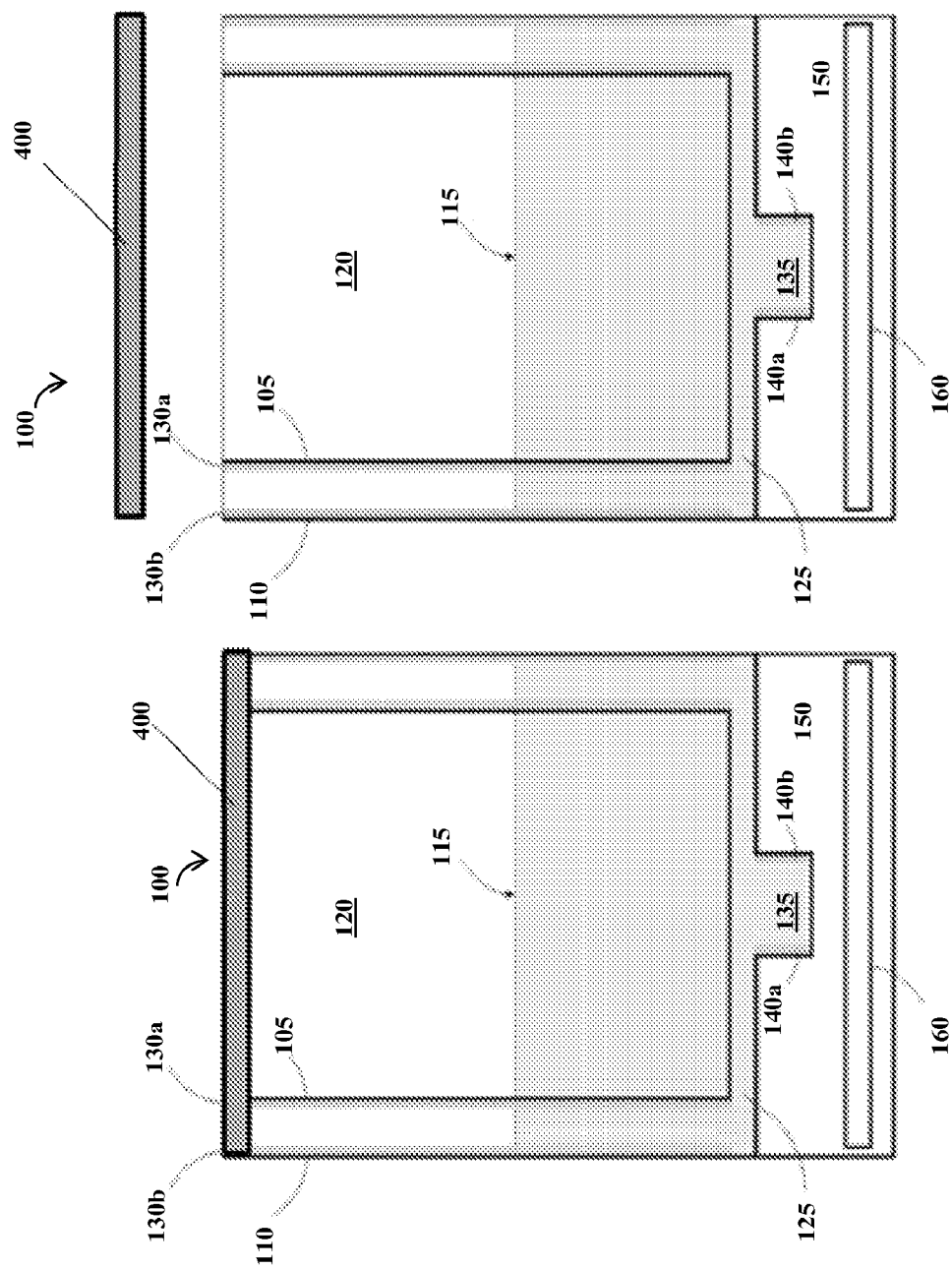
FIG. 5 is a cross-sectional view of a fifth embodiment of the fluid analysis device, including a cover.

In one specific aspect, illustrated in FIG. 5, the device 100 can be adapted to include a cover or cap 400 for storing or transporting the fluid 115, or combinations thereof, for example to contain fluid until it is disposed. Additionally the at least one handle 165 (shown in at least FIG. 1, 2a-c, and 4a-b) may be coupled to the outer wall 110 by a rotatable coupling, (e.g., bearing, swivel, etc.), allowing the device 100 to remain upright at all times during use.

Regarding the specific shape, design, and dimension of the fluid receipt chamber 120 or cups, nearly any shape, design, or size can be used which is suitable to achieve a desired purpose. Such shape and size considerations may be specified based on the intended purpose. Although the text and drawings herein refer to the fluid receipt chamber 120 as a cylinder, other shapes are possible such as those having square, rectangular, or other cross-sectional shapes as well as those having straight and tapered walls. Fluid receipt chambers 120 with straight walls provide linear changes in capacitance with increases in fluid volume, although adjustments may be made for chambers having tapered walls to account for the changes in volume due to the tapered shape.

In the embodiment in which the fluid receipt chamber 120 consists of two concentric capacitive cylinders, described in reference to FIG. 1, the geometry of the device 100 has been optimized based on factors including those listed below. Various embodiments of the disclosed invention may meet one or more of the following criteria:
1. Maximize the signal-to-noise ratio by maximizing the change in voltage with an incremental change in fluid height.
   a. This is achieved by minimizing the diameter of the outer capacitive cylinder (assuming a constant volume) and making the device taller. However, ergonomic considerations, device storage, and cleaning must also be taken into account in determining an appropriate diameter and height. The ratio of height to diameter of the fluid receipt chamber is approximately 1:1 to 3:1 in certain constructions. In other constructions, the ratio is approximately 11:7, although other ratios are possible.
   b. In certain embodiments, this may be achieved by minimizing the spacing between the two concentric cylinders (e.g., approximately 3-10 mm). This effectively increases the capacitance of the primary (first) sensing element, therefore increasing the overall signal. However, too small of a spacing may make the device difficult to clean and may increase error due to capillary action between the plates.
2. Linearize the voltage-fluid height relationship (or at least approach a linear relationship).
   a. This is achieved by maximizing the fluid spacing between the two concentric cylinders, which minimizes the contribution of the insulative layer(s) in the overall capacitance of the system.
3. Minimize the contribution of any insulating layer(s) on the overall capacitance.
   a. This is achieved by making the capacitance of any insulating layer(s) much greater than the capacitance of the fluid (at least 3-5 times greater). This is done geometrically by making the fluid gap significantly larger than the insulating layer.

Taking into account all of these considerations, the following geometric ranges were found to be suitable for this specific embodiment. The first capacitive element may have an outer diameter of about 3-5", a height of about 4-6", and a capacitor spacing of about 0.25-1", and the second capacitive element may have a height, width, and spacing of about 0.1-1".

In some embodiments, the second capacitive element can have horizontally-oriented plates (i.e. the plates are parallel to the bottom surface and perpendicular to the side walls of the fluid receipt chamber 120). In other embodiments, the second capacitive element can have the same configuration (shape, dimensions, etc.) as the first capacitive element, although the second capacitive element is generally located at the bottom of the inner fluid chamber so as to be filled prior to the first capacitive element. Furthermore, the floor of the fluid chamber can be sloped so as to ensure that recess 135 in which the second capacitive element is located is filled even when the device 100 is tilted. The recess 135 and second capacitive element may be located at the bottom of the fluid receipt chamber 120 or, as shown in FIG. 1, below the bottom surface of the fluid receipt chamber 120.

The first and second capacitive elements can be made from any suitable capacitive material. Such materials can include iron, titanium, nickel, chromium, copper, aluminum, silver, silicon, and any other suitable metals or alloys thereof. Additionally, the conductive material can include a conductive polymer such as polyfluorenes, polyphenylenes, polypyrenes, polyazulenes, polynaphthalenes, polycarbazoles, polypyrroles, polyindoles, polythiophenes, polyanilines, polyazepines, and any other suitable conductive polymer or combinations thereof.

In some embodiments, the walls of the device 100 can be adapted to insulate or protect one or more of the capacitive elements 130a, 130b, 140a, 140b and various other components of the fluid analysis device 100 from the fluids 115 being measured. In general, at least one of each of the pairs of the capacitive elements 130a, 130b, 140a, 140b is electrically insulated from the fluid 115 in order to hold an adequate charge and to prevent the plates from discharging through the fluid 115. This electrical insulation may be provided by a non-conductive wall or by an insulating coating applied to the capacitor plate.

The walls or insulating coating can be made of any suitable material known in the art that can protect the capacitive elements, electrical circuitry, and other components from corrosion and damage due to contact with the fluid. Examples of materials that can be used in the manufacture of the walls can include without limitation, ceramics, glass, polymeric materials such as polyurethane, polyethylene, polypropylene, other plastics, and the like. Likewise, the housing of the device 100 can be made of any suitable materials which allow construction and accurate operation of the device as intended. In some embodiments, the walls of the device may also be coated with a hydrophobic or antimicrobial coating to reduce buildup on the walls and reduce the risk of bacterial infections.

Figure 6:
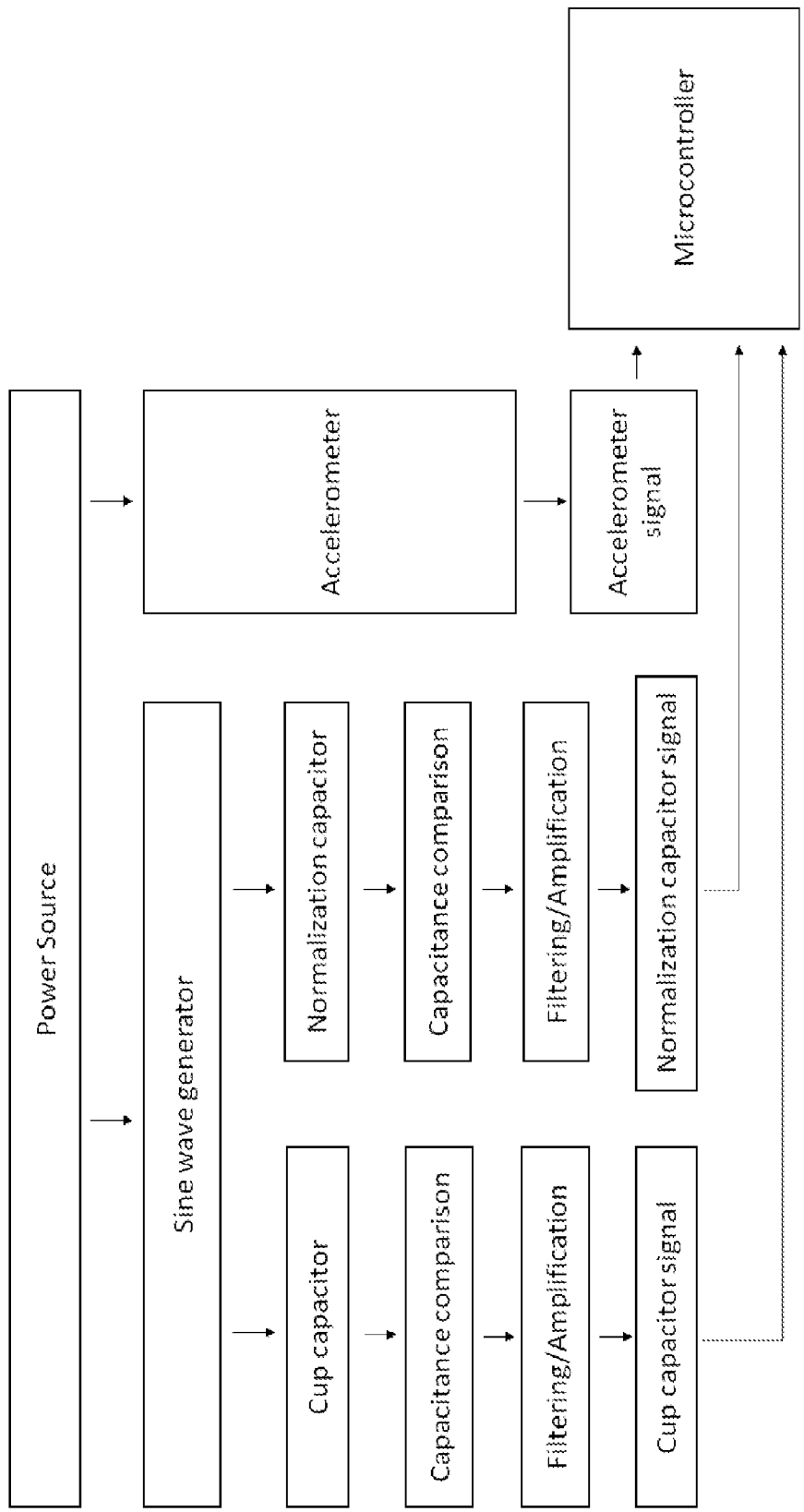
FIG. 6 is a block diagram illustrating an example of a system for generating and measuring electrical signals.

FIG. 6 shows an example of a system used to obtain and measure the signals of exemplary electrical components. A power source (e.g. a battery) provides power to the electronics unit 160, which includes a sine wave generator for providing a sinusoidal voltage to the capacitive plates. The power source also provides power to an optional tilt sensor such as an accelerometer or inclinometer. The signals from the pairs of capacitive plates are compared to determine changes in capacitance since the last reading and the signal is optionally filtered and amplified. The resulting "cup capacitor signal" or first capacitive element signal and "normalization capacitor signal" or second capacitive element signals are fed to the controller/microcontroller (along with the signal from the tilt sensor, if present).

Figure 7:
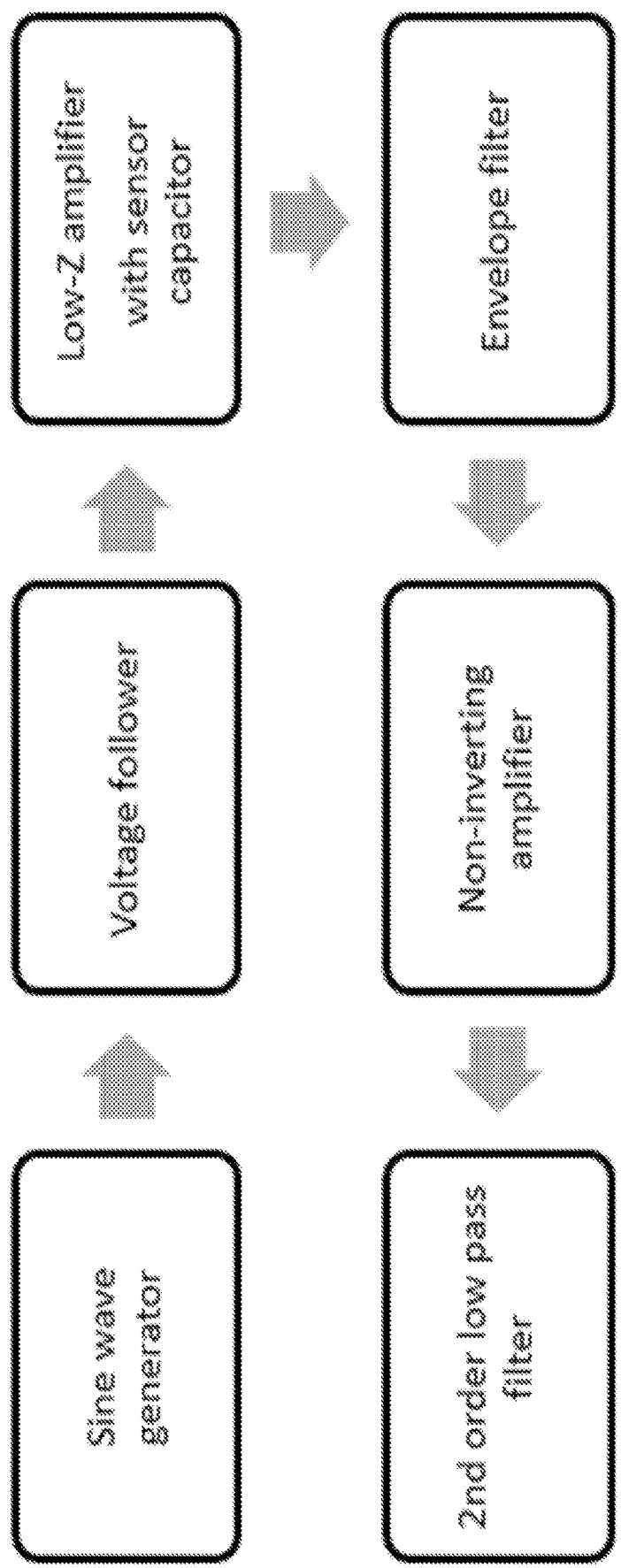
FIG. 7 is a block diagram showing a process used to measure changing signal in a first capacitive element.

When fluid is introduced into the fluid receipt chamber, the fluid displaces air as the dielectric in the first capacitive element and the second capacitive element. The second capacitive element is generally disposed at or near the bottom of the fluid receipt chamber so that it is completely submerged in the fluid before the first capacitive element. The capacitance of the second capacitive element may be used to correct for differences in the dielectric of the fluid (e.g. dielectric differences between different fluids or from different fluid samples such as different urine samples). As the level of fluid within the fluid receipt chamber increases, the capacitance of the first capacitive element increases as air is replaced as the dielectric by the fluid. The capacitance of the first and second capacitive elements can be determined by application of a sinusoidal voltage to each of the pairs of plates of the respective elements. An example of a process and circuitry used to measure and process the dynamic signal of the first capacitive element and the second capacitive element as fluid fills the chamber is shown in FIG. 7. In this example, the capacitive element is located within a low impedance ("Low-Z") amplifier. The oscillating voltage from the sine wave generator is fed through a voltage follower and then to the Low-Z amplifier including the sensor capacitor. The output of the sensor capacitor may be subjected to one or more of an envelope filter, a non-inverting amplifier, and a second-order low pass filter. This process is exemplary by nature, and one of skill in the art will recognize this may be accomplished in other ways.

Figure 8:
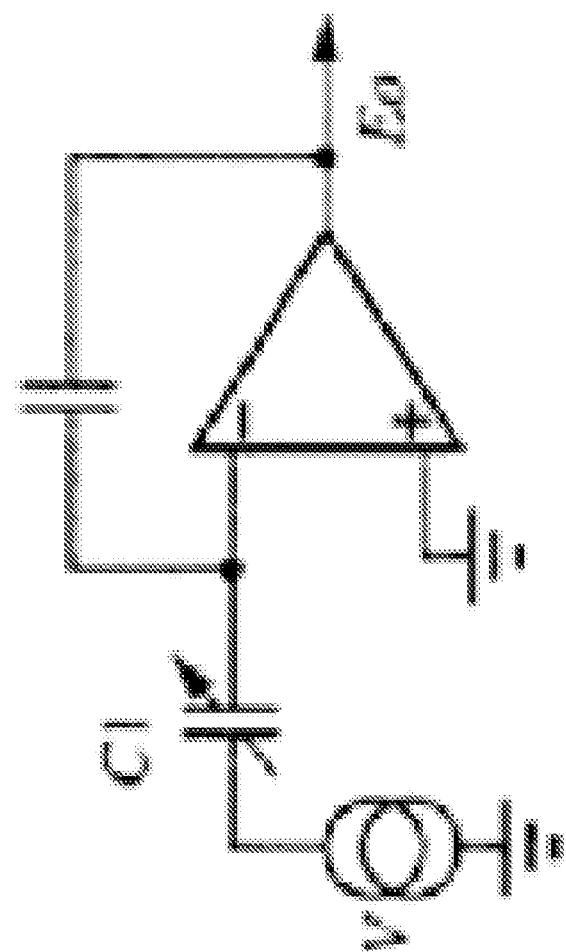
FIG. 8 is a schematic of a Low-Z amplifier from FIG. 7.

FIG. 8 shows the details of a Low-Z amplifier such as that referenced in FIG. 6, where the amplifier measures a linear voltage change based on changes to C1, where C1 is the first or second capacitive element and the change in capacitance is directly related to the voltage measured.

Although the Low-Z amplifier has a linear relationship between changes in C1 and voltage, other components of the circuitry and the added capacitance of the insulating layer(s) may contribute to make the overall relationship non-linear. For this reason, a non-linear calibration curve may be used to relate the voltage to a particular volume measurement. The calibration curve is created by placing known volumes of fluid into the first capacitive element and recording the voltage. This process is repeated with incremental volumes of fluid until the first capacitive element is completely filled.

The first and second capacitive elements in the device 100 can be used to measure various fluid flow characteristics or fluid parameters, such as flow rate and volume. Some non-limiting examples of other fluid flow characteristics that can be measured by the current device are voided volume, voiding time, average flow rate, maximum flow rate, and combinations thereof where the fluid can be urine or any other suitable fluid. The device 100 can also be adapted to provide a linear analysis of the flow rate/voiding time in order to determine a voiding pattern. In one aspect, the device can measure fluid volume. In one aspect, the device can measure the fluid flow rate. In one aspect, the device can measure urinary output volume. In one aspect, the device can measure urinary flow rate. In one aspect the device can measure maximum urinary flow rate.

Volume: Instantaneous volume measurements (i.e. amount of liquid in the device at the time of the data measurement) are determined by converting the voltage output from the sensor circuit into volume readings using a dielectric specific calibration curves.

Flow rate: Determined by subtracting two consecutive volume measurements and dividing by the sampling time in between the measurements. Noise is reduced by two low pass filters in the circuit and a moving average after data collection.

Max flow rate: Determined by taking the maximum value from all of the flow rates Average flow rate: Determined by taking the average of all of the flow rates above 0.5 mL/s.

Voiding time: Determined by counting the number of flow rates were greater than (0.5 mL/s) and multiplying by the time in between each sample.

Max volume: Determined by taking the maximum volume measurements used to calculate other flow parameters The dielectric properties of fluids may vary. For example, the dielectric properties of urine vary from patient to patient and even between voids for a given patient. These changes in dielectric properties affect capacitance measurements and, therefore, affect volume and flow rate calculations. The primary role of the second capacitive element is to normalize the data collected with the first capacitive element. This can be accomplished when the dielectric of the second capacitive element (which is initially air) is completely replaced with the fluid introduced into the fluid flow measuring device. The second capacitive element must be positioned and sized such that it is most likely to become completely filled during a void. Once the second capacitive element becomes completely filled, its reading provides a useful correlation between volume and voltage that can be used to normalize all subsequent readings taken by the first capacitive element. This normalization can be done in a number of ways. These are, but not limited to, the following:

1. Using the voltage measurement from the second capacitive sensor, along with theoretical relationships well known to the art to calculate the actual dielectric value of the current fluid in the device. Then apply this dielectric constant to the specific geometric configuration of the first capacitive sensor.

2. Having a single calibration curve for a specific fluid dielectric, and then adjusting this curve to account for any differences in the current fluid dielectric using a theoretically or experimentally derived relationship.

3. Experimentally generating calibration curves or look-up tables for a variety of dielectrics spanning the range of physiological urine. The reading from the second capacitive element can then be used to look up and apply the calibration curve that is closest to the current fluid in the device.

In one aspect, the first and second capacitive elements can be run as separate measurement circuits in parallel with one another. The capacitive elements can be cylindrical capacitors, parallel plate capacitors, thin film capacitors, or any other suitable capacitor. In one aspect, the first and second capacitive elements can both be the same type of capacitor.

In another aspect, the first and second capacitive elements can be of different capacitor types.

The specific layout of the capacitors may also vary. The capacitors may be symmetrically disposed within the device, or may have an asymmetric pattern. In some embodiments, two capacitors are used. In other embodiments, at least three capacitors are used and disposed at varying locations along the walls of the device.

In various embodiments, the disclosed device 100 is relatively insensitive to being tilted and can correct for any tilt or change in orientation relative to a vertical axis. This characteristic enables the device to be hand-held and portable (e.g. for at-home use) yet still maintain accuracy. Various means can be employed so that tilting of the device does not affect capacitance measurements. In general, the requirement for a device with concentric capacitive plates to be insensitive to tilt is that there should be a linear relationship between fluid height and the measured voltage, i.e. the derivative of voltage with respect to height is constant. That is to say that adding x amount of fluid always results in the same increase in fluid height. In general, a container with a constant cross-sectional area (bore) is expected to have this characteristic.

Should these requirements not be met, additional measures could be made to correct for any non-linearities so that the device 100 can be relatively insensitive to tilt. These additional measures include, but are not limited to, using an orientation or tilt sensor (e.g. inclinometer, accelerometer, gyro or any other suitable tilt or orientation measuring device). The tilt sensor may be located on the base 150, on a wall 105, 110, fixed into the body of the device, or placed at other locations that do not prevent adequate tilt measurement. The tilt sensor is configured to directly measure the amount or degree of tilt. However, alternate additional measure include using a non-linear calibration, positioning capacitive plates in the middle of the device 100 where tilt is less likely to affect fluid height, changing the effective area of the parallel plates as a function of height, and/or varying the spacing of the concentric plates as a function of height.

Furthermore, additional configurations not involving concentric plates could also be employed to obtain a device that is insensitive to tilt. As one example, having two separate fluid height capacitive sensors on opposing sides of a constant bore receptacle would also suffice.

In general the capacitive plates (including a single pair of plates or multiple pairs of plates) which make up the first capacitive element (i.e. those which line the fluid receipt chamber 120 and provide measurements of the increase of fluid height) are arranged in a symmetrical pattern around the perimeter of the fluid receipt chamber 120. By arranging the capacitive plates in a symmetrical pattern, when the device 100 is tilted, any increase in capacitance on one side of the fluid receipt chamber 120 arising from a greater amount of the gap between the plates which is occupied by fluid is offset by an approximately equal decrease in capacitance on the opposite side of the fluid receipt chamber 120.

Figure 9:
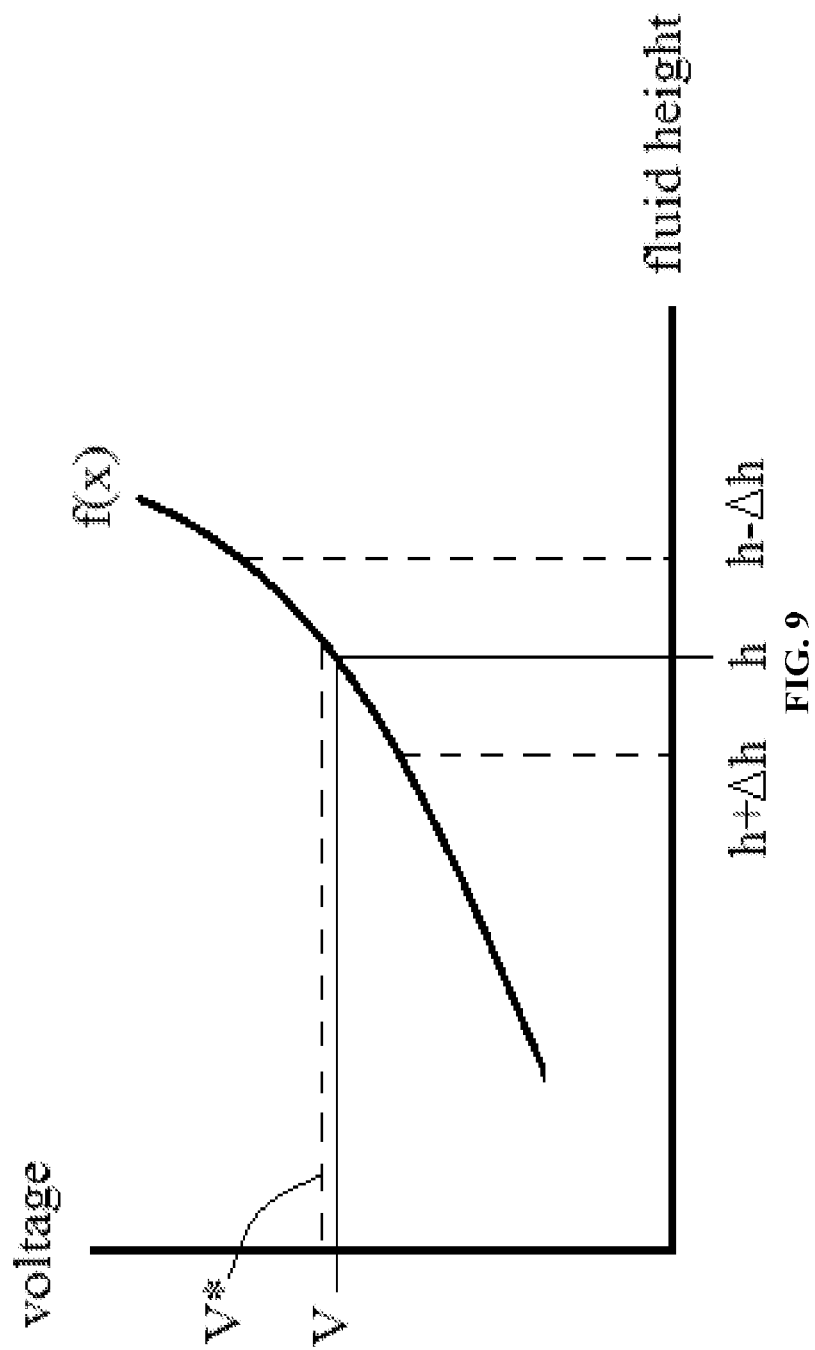
FIG. 9 is a graph illustrating a theoretical implementation of using a tilt sensor to correct for any changes in measured voltage when the device is tilted.

One particular embodiment of the device uses an accelerometer to correct for any tilting during use. An exemplary implementation of the accelerometer and a corresponding algorithm is shown in FIG. 9. The algorithm, in this example, accounts for a device with a cylindrical capacitor having a known radius 'r' and non-linear calibration f(x) which maps fluid height 'h' to voltage 'V'. As the device is tilted to an angle 'θ' relative to vertical, one side of the capacitor is exposed to a fluid height 'h−Δh' while the opposite side is exposed to a fluid height 'h+Δh' resulting in a perturbed voltage reading 'V*' where $$(V^*)(2\Delta h) = \int_{h-\Delta h}^{h+\Delta h} f(x)dx \text{ and } \Delta h = r^* \tan\theta$$

Since V* is the actual voltage read by the device, θ is the tilt measured by the accelerometer, 'r' is a manufactured parameter, and f(x) is a predetermined calibration, the above integral can be solved for the actual fluid height 'h'. This approach enables a precise reading of fluid height even in the absence of a linear voltage relationship. Of course, should the capacitor be designed to have a linear relationship between fluid height and voltage, such an integral would be unnecessary as the V* would be equal to V when the device is tilted.

The circuitry used to operate the first and second capacitive elements and any other desired sensors and electrical components can be adapted or configured in any way suitable for the intended purpose of the device. These circuitry components are generally known in the art and are contemplated as useful in the current technology.

Additionally, the device 100 can be adapted to include a variety of additional sensors suitable for a specific application or set of applications. The fluid analysis device 100 can utilize optical, chemical, or other measurement techniques to detect or measure properties in fluid or urine that are normally found in current fluid or urine analysis. These properties include, but not limited to, at least one of the following: weight, specific gravity (density), temperature, glucose, blood (hemoglobin), presence of proteins, leukocytes, acidity/alkalinity (pH), urobilinogen, bilirubin, presence of nitrates, sodium chloride, presence of ketones, and beta hCG (pregnancy). Any suitable sensor may be used with the present technology and can be selected based on the intended sensing to be performed. Exemplary sensors include, without limitation, temperature sensors (e.g., thermocouple, thermistor, infrared sensor, etc.), electrochemical, potentiometric, amperometric, conductometric, chemicapacitive, chemiresistive, photoionizing, a field-effect transistor, a physical transducer, an optical transducer, biochemical, affinity-based, thermochemical, optical, piezoelectric, or any other suitable sensor. In some embodiments, the chemical sensor(s) can have a single recognition site or a plurality of recognition sites depending on the degree and type of sensitivity desired in the sensor. The plurality of recognition sites can be configured to detect a plurality of signals. The device can include a single sensor or a plurality of sensors. Where a plurality of sensors is used, the sensors can be the same type of sensor or they can be different types of sensors. In various embodiments, the sensors or portions thereof may be incorporated into the electronics unit 160. In certain embodiments, portions of the sensors which interact directly with the fluid are housed in or adjacent to the fluid receipt chamber and are electrically coupled to the electronics unit 160 using suitable electrical connections.

In various embodiments, a temperature sensor (which can include but is not limited to a thermocouple or an infrared sensor) can be incorporated into the fluid analysis device. In one particular embodiment, the temperature sensor includes a thermocouple disposed at the bottom of the fluid receipt container which is operably coupled to the electronics unit 160. The electronics unit 160 obtains fluid temperature data from the sensor; the electronics unit 160 may then store the fluid temperature data, perform calculations with the data, and/or transmit the data to an external device for storage and/or further processing.

The additional data obtained from temperature and other sensors, in concert with the fluid flow data, may be used individually or in any combination thereof to identify anomalous health conditions and/or facilitate the basis for trending health conditions and/or artificial intelligence to assist in the early detection and/or treatment of pending negative and/or detrimental health conditions.

In some embodiments, the disclosed measurement and analysis device may include one or more sensor components that may be used in conjunction with the disclosed methods. This sensor component can be inserted before or after fluid is added to the device.

Figure 10:
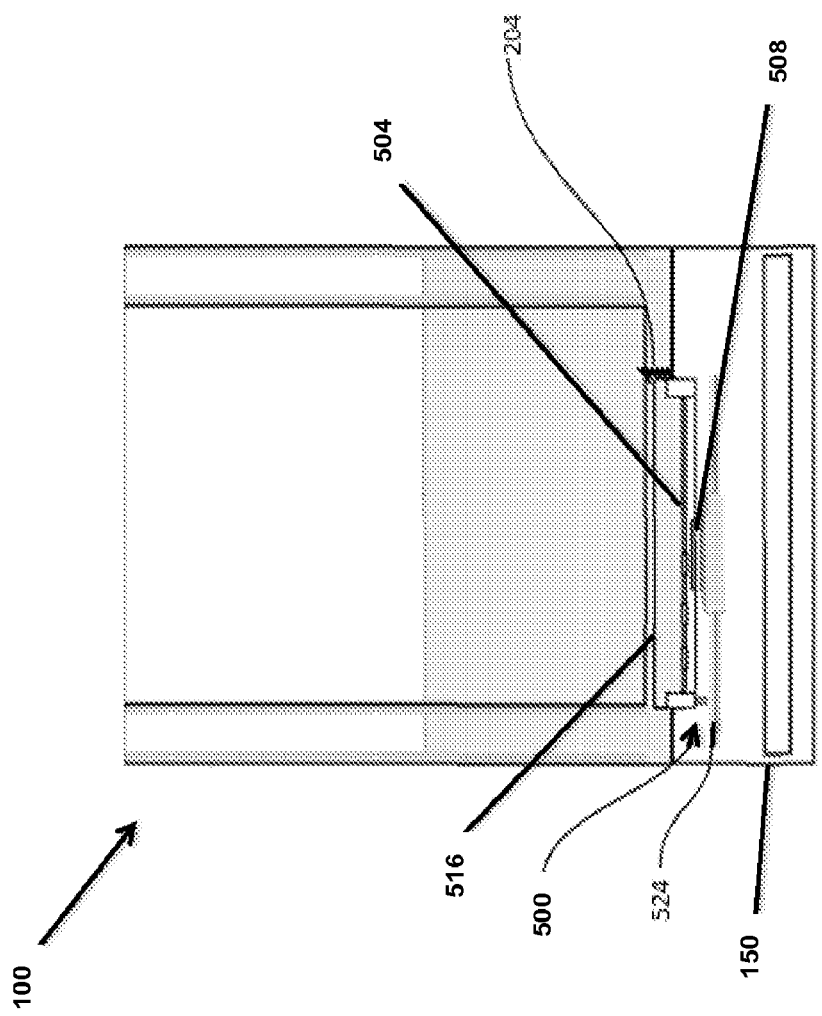
FIG. 10 is a cross-sectional view of a sixth embodiment of a fluid analysis device with a sensor component.
Figure 11:
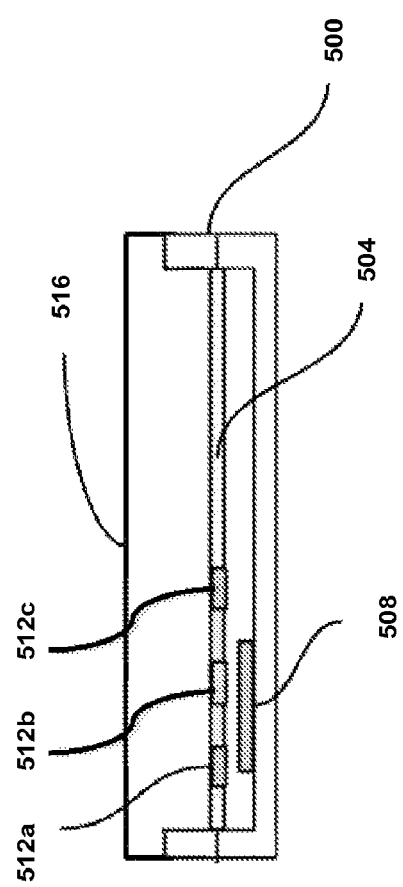
FIG. 11 is a cross-sectional view of the sensor component of the device in FIG. 10.

In one embodiment, illustrated in FIGS. 10 and 11, additional properties of the collected fluid can be measured by including a sensor component 500 (which may be disposable or reusable) into or near the bottom of the fluid analysis device 100, generally prior to a fluid such as urine entering the device 100. In some embodiments, the sensor component 500 may be placed in a slot at the bottom of the device 100 that is configured to hold the component 500 securely using at least one latching feature 204. In certain embodiments, the sensor component 500 may form part of the bottom of the device 100 and would therefore be secured in a fluid-tight manner into the device 100. In other embodiments, the sensor component may alternatively lay flat on the bottom of the device 100 (which may be or include a transparent portion or portions through which readings may be obtained), parallel to the base 150, or vertically, perpendicular to the base 150, or any other orientation.

The sensor component 500 may house a reagent strip 504 (e.g., Areta 10 Parameter (10SG) Urinalysis Reagent Strips, although other types of strips are also possible) that can detect and measure at least one of the properties described above, as well as at least one sensor 508 (e.g. an optical sensor) configured to monitor the reagent strip 504 and send information (e.g., 12-bit RGB code) relating to portions 512*a*, 512*b*, 512*c* of the reagent strip 504 (FIG. 8). In various embodiments, the portions 512*a*, 512*b*, 512*c* of the reagent strip 504 may correspond to one or more sensor pads, each of which may be configured to sense a different analyte, where each sensor pad will have a detectable change in a property (e.g. color) corresponding to the level of the analyte that is present. For example, if the portions 512*a*, 512*b*, 512*c* change to a different color depending on the concentration of a particular analyte present in the sample, then a sensor 508 is provided which is capable of detecting the colors of the portions 512*a*, 512*b*, 512*c*. The sensor component 500 may include a covering 516 over the reagent strip 504 to limit or block outside light while allowing urine or other sample material to interact with the portions 512*a*, 512*b*, 512*c* of the reagent strip. In some embodiments, the optical sensor 508 may include a light source such as an LED, which may be either formed integrally with or provided externally to the sensor 508 to ensure lighting is sufficient and consistent for each reading. The light source emits light in conjunction with the sensor 508 obtaining data from the one or more portions 512*a*, 512*b*, 512*c*. To the extent that the readings from the portions 512*a*, 512*b*, 512*c* may change as a function of time, the portions 512*a*, 512*b*, 512*c* in certain embodiments may be read several times (e.g. once every 1-60 seconds) over a given time period (e.g. from 10 seconds up to 10 minutes following initial wetting of the sensor component 500).

Figure 12:
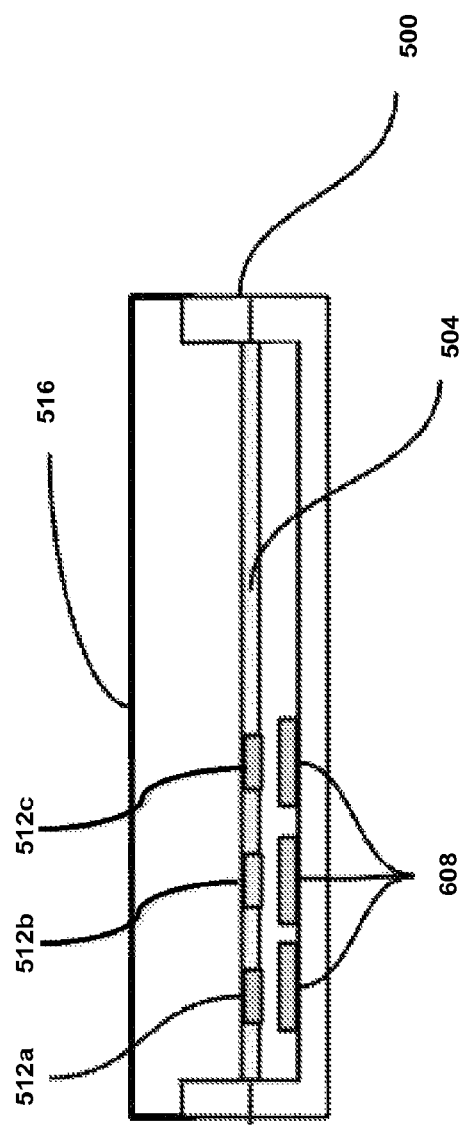
FIG. 12 is a cross-sectional view of an alternate embodiment of the sensor component.

Referring to FIGS. 10 and 11, in one embodiment a single optical sensor 508 may be provided to read multiple portions 512*a*, 512*b*, 512*c* on the reagent strip 504, where the optical sensor 508 may be moved along an axis by a linear actuator 524 in order to read each portion 512*a*, 512*b*, 512*c* of the reagent strip 504. However, in alternate embodiments such as the one illustrated in FIG. 12, the sensor component 500 may include an array of sensors 608 (e.g. optical sensors) disposed at regular locations adjacent to each of the portions 512*a*, 512*b*, 512*c* on the reagent strip 504, each sensor being configured to read a corresponding portion of the reagent strip 504. In another embodiment, the sensor component 500 may include a single sensor unit capable of reading multiple portions of the reagent strip 504 without moving (e.g. a linear CCD).

In other constructions, the sensor component 500 may be a reusable and optionally sterilizable attachment. In such embodiments, the reagent strips 504 may be detachably coupled to the component 500 to allow for insertion and removal. Furthermore, the reagent strips 504 may be housed in a cartridge configured to detachably couple to the sensor component 500, allowing the user to remove the cartridge and replace the reagent strips 504 before inserting the cartridge back into the sensor component 500. Alternatively, the reagent strips 504 may couple directly or indirectly (e.g., through the use of a cartridge) to the device 100 (generally at or near the bottom), while the optical sensors may be included in the base 150 (e.g. integrated with the electronics unit 160, see below).

In operation of a device according to the illustrated embodiments, an individual may void directly into the device 100 or urine may be placed into the device 100 so as to contact the reagent strips 504. The urine is then removed from the device 100 and the reagent strip 504 is analyzed. In certain embodiments one or more readings will be taken within a limited time period determined by the particular sensing portions 512*a*, 512*b*, 512*c* being used (e.g. within about two minutes) following contact between the portions 512*a*, 512*b*, 512*c* and a fluid such as urine. In certain embodiments, to read the portions 512*a*, 512*b*, 512*c* the linear actuator 524 will move optical sensor 508 allowing the sensor to read each portion 512*a*, 512*b*, 512*c* of the reagent strip 504 in order to generate a signal indicating information (e.g., 12-bit RGB code or other signal, as appropriate) for each portion 512*a*, 512*b*, 512*c* of the reagent strip 504. The signal may then be processed within the device 100 or may be transmitted to an external device for further processing. For example, the signal may be sent to either the controller disposed within base 150 or to an external device to map each RGB code to the closest tabulated color and associated metric (e.g. using a basic minimization algorithm or other suitable calculations). However, other processing techniques have been contemplated as useful.

In certain embodiments, if only small amounts of urine are introduced, the device 100 may be tilted in a way to cover the reagent strip 504 with urine thus exposing all parts of the reagent strip 504 to the urine; once the reagent strip 504 and the portions 512*a*, 512*b*, 512*c* of the reagent strip 504 have been saturated, the remaining steps of the process for obtaining readings would be generally unchanged from what is described herein. Additionally, the scanning of the reagent strip 504 may be performed before the urine is removed from the fluid analysis device 100, or after the sensor component 500 is separated from the device 100.

In other embodiments, combinations of more than one sensor component used for measuring the properties listed above may be employed on a single device 100. These sensor components may each include reusable or disposable components, or at least may contain some reusable or disposable features. In other embodiments, the reagent strip 504 may be integrated into the bottom of the device 100, generally in conjunction with embodiments in which some or all of the device 100 (e.g. one or more parts of the fluid receipt chamber) is intended to be disposable.

In addition, the device 100 may include an electronics unit 160 having number of other modules or components in order to carry out its intended operation. At a basic level, such components can include a power source or module, a data collection module, a memory or data store, a communication module, and a controller module. Additionally, in some embodiments, the device can include a user interface (such as a graphical user interface) configured to allow the user to operate the device and/or view testing results directly thereon.

The power module is configured to power the device. Any power source sufficient to adequately power the device may be used. Batteries, capacitors, and/or other power sources that don't interfere with any of the sensors or other measuring components of the device may be selected in view of the device's intended purpose and duration of operation. In one aspect, the power module can include a battery. In one example the battery can be a rechargeable battery. Other components can be included in the power module, for example, wires and electrical connections required to operably connect the battery to other modules within the fluid analysis device that require power for their operation. In one specific example, the power module may include components that inductively charge the battery when exposed to an adequate external influence, such as a wireless or magnetic influence. In such embodiment, if charging of the battery is necessary or desired, the proper external influence can be brought within a sufficient range to operate the inductive components and charge the battery without physically accessing the device. The battery can also be recharged using a physical connection to an outlet, USB port, or other suitable power source.

The data collection module can be operatively coupled to the device in a manner sufficient to receive capacitive data, and is configured to collect and store capacitive data. Typical components of a data store may be used, such as readable writable memory, connections to power, and suitable input/output (I/O) connections to other device components or modules. Those of ordinary skill in the art will understand the assembly and operation of such components.

The communication module can be configured to communicate with a peripheral or external device, such as a computing device (i.e. computer), mobile device (e.g. smart phone or tablet), or cloud database, in order to transmit and/or receive information. Typical components for such a module may be used. In one aspect, the data communication module can include components to facilitate a physical connection between the fluid flow measurement device and a remote device. In one aspect, the communication module may include a wireless transmitter/receiver capable of wirelessly communicating with the remote device. Nearly any wireless frequency, range, protocol or type can be used, for example short-wavelength radio waves in various bands, such as Bluetooth®, local area wireless technologies, such as WiFi, WiMAX®, or other IEEE 802.11 protocols, cellular, including GMA and CDNA, radio, electromagnetic, or any other suitable method of wireless communication. In one embodiment, the wireless transmitter/receiver can be a low power consumption device, for example, Bluetooth® low energy (LE).

Figure 13:
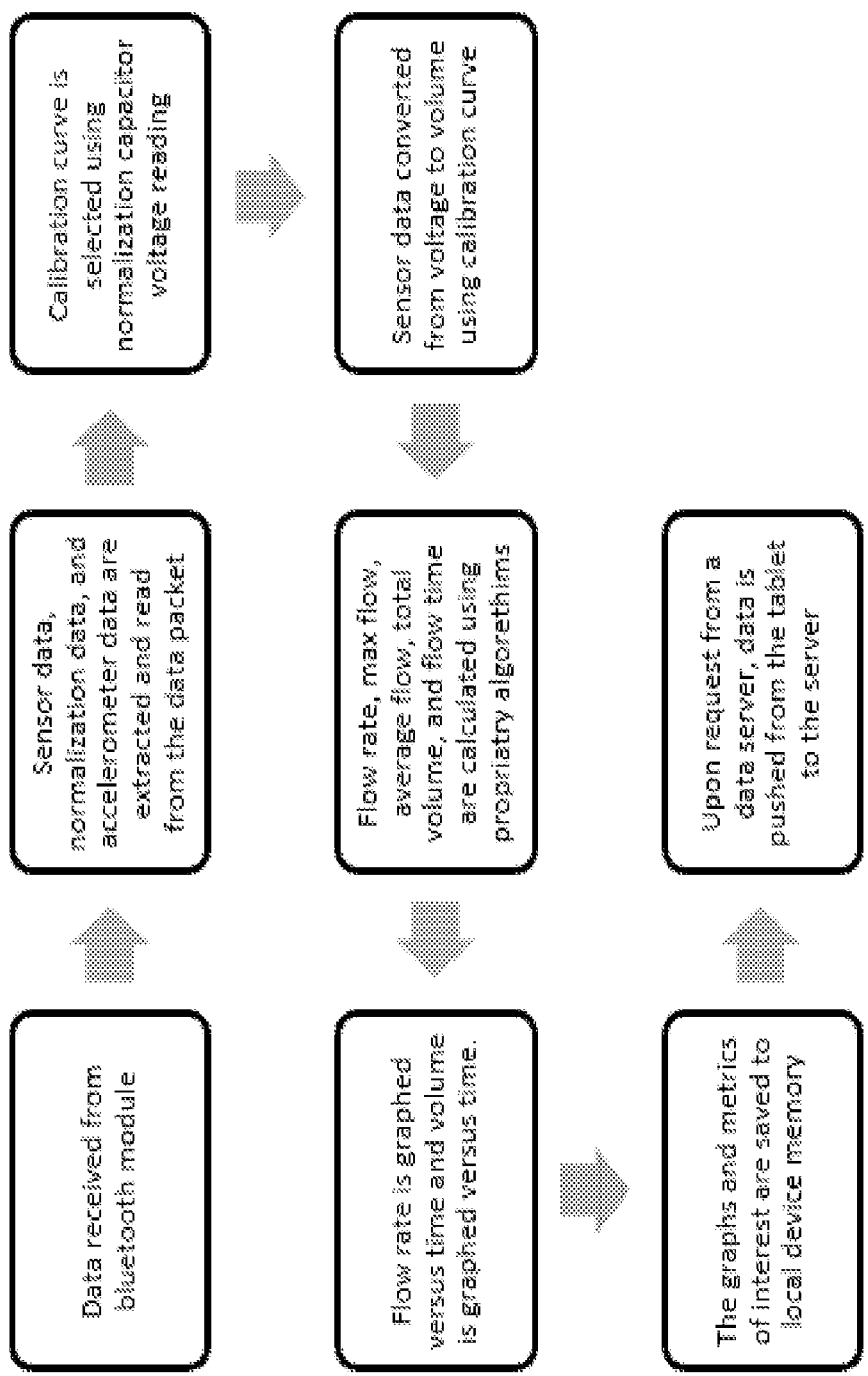
FIG. 13 is a block diagram of the control software currently used to display flow on a peripheral device in real-time.

A block diagram of the control software currently used is shown in FIG. 13. It should be noted that, while certain specific steps and protocols are illustrated, other steps and protocols may be substituted, removed, or added in place of steps and protocols shown in FIG. 9 such as those mentioned above and others generally known in the art.

Additionally, the communication module can be adapted to provide a biofeedback signal based on capacitive or other sensor data that alerts the user to a significant medical condition. The communication module can transmit a signal to a remote device, turn on an LED associated with the device, or provide any other suitable signal or alert for the user to seek medical assistance.

The controller module can be configured to control the operation of the fluid flow measuring device, including all aspects of device activity, data collection, and communications. The controller module is operatively coupled to the other device modules as necessary to affect such control. The controller module generally includes one or more processors and memory and is equipped with program logic sufficient to control all aspects and function of the device.

In one embodiment, the program logic of the controller may include instructions to control the communications module based on device activity. For example, the controller module can activate or deactivate the communication module and/or other device components upon receiving an indication of a change in capacitive or other sensor measurements. In an additional aspect, deactivation of the communications module can occur based on an amount of time that has lapsed since its activation. Such an amount of time can be programmed into the controller as part of the program logic and selected by a user in view of the desired purpose and operation of the fluid flow measuring device.

In some embodiments, the computing and logic components as well as controller elements can be located in a device separate from the fluid flow measuring device, and which is in communication therewith. In such another embodiment, the devices can form system for measuring fluid characteristics. The system can include the urinary flow measuring device as recited above and a computing device in communication therewith. The computing device can be a hand-held device, such as a tablet or smart phone, a server, a personal computer, or other suitable device. Additionally, the computing device can include a power module, a controller, a data receipt module, and a memory module.

The power module and controller can operate as described previously. The data receipt module can be operatively connected to the fluid flow measuring device. It can be adapted to receive data generated by the fluid flow measuring device, whether data transmission is wireless, via cable, or via a removable storage device. The data receipt module can remain in a passive receiving mode until prompted by the measuring device. This module can use standard computing components known in the art.

The memory module can be operatively connected to the other modules of the computing device and can be adapted to store the data received via the data receipt module. Typical components of a data store may be used, such as readable writable memory, connections to power, and suitable input/output (I/O) connections to other device components or modules. Those of ordinary skill in the art will understand the assembly and operation of such components.

A remote device used in connection with the fluid analysis device can be any number of computing devices that are capable of wirelessly communicating with the fluid flow measuring device. As previously mentioned, exemplary devices include without limitation desktop computers, mobile devices, such as smart phones, laptops and tablets. Cloud or other internet connected databases can also be used. In addition to a wireless transmitter/receiver, such devices may also include processors, memory, and I/O components necessary for a user to operate the device, among others. Generally, components sufficient to report data received by the remote device to the user can be included. Such computing devices are well known in the art. In one aspect, the remote device can be equipped with an application that is configured to display, quantify, and interpret data received from the fluid flow measuring device. In some aspects, the remote device and/or the program logic thereon can control, program, or otherwise input information into the fluid flow measuring device.

Figure 14:
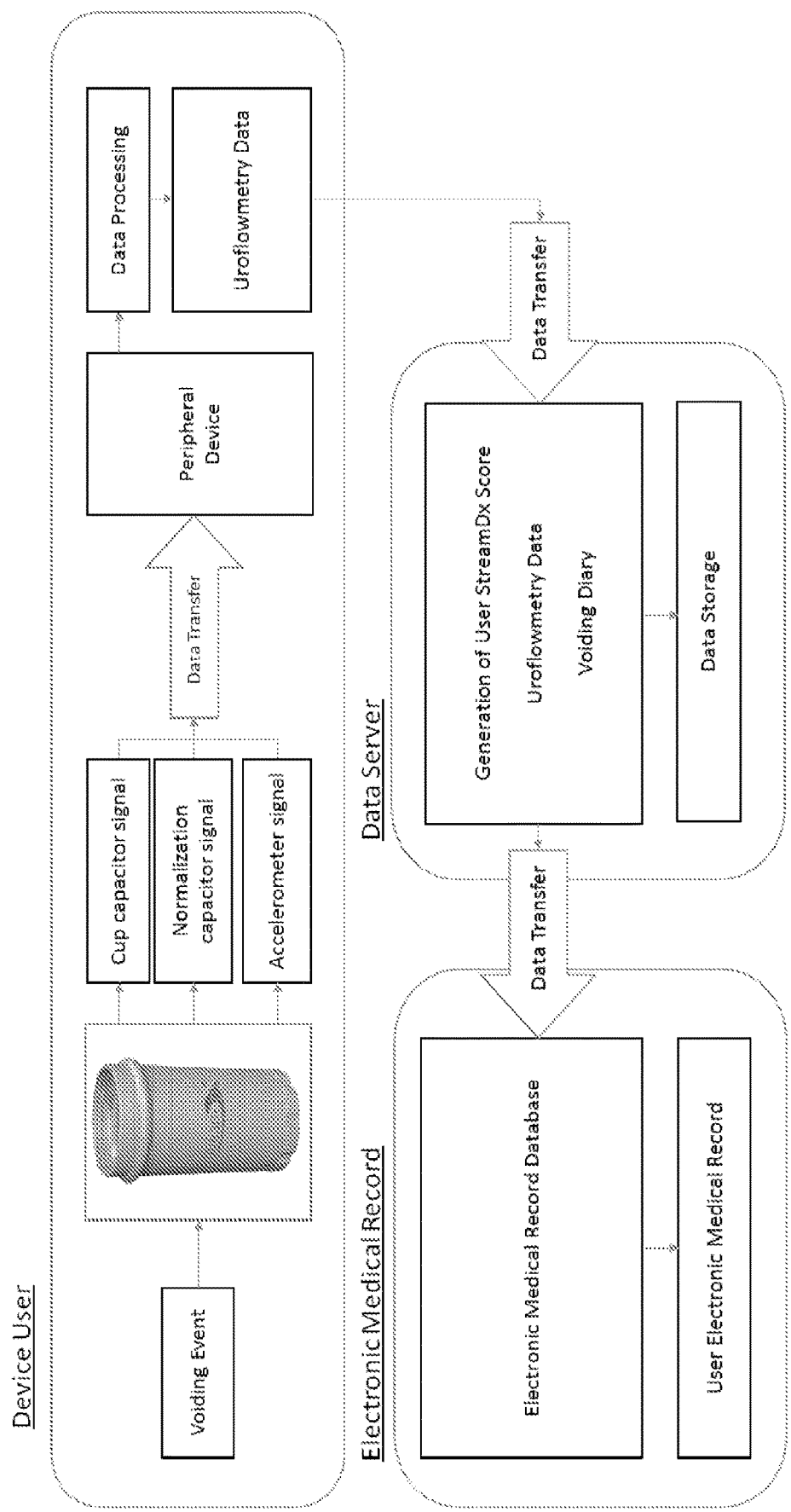
FIG. 14 is a block diagram of a method for operating the device in conjunction with a peripheral device, a data server, and an Electronic Medical Record.

In operation, the above-recited devices and systems are capable of performing a number of useful methods. In one embodiment, shown in FIG. 14, a method of measuring a fluid flow characteristic is described. This method can include a voiding event in which fluid is introduced to the device, and then passing the fluid through at least two capacitive elements. Each capacitive element can include a plurality of plates made from any suitable material, such as those previously described. Additionally, the method can be executed while tilting the capacitive elements from an upright position without significantly affecting measurement of fluid flow characteristics since components, such as a tilt sensor, may be used to correct for the tilt. Information from the first capacitive element can be normalized using information collected from the second capacitive element. The information collected using this method can be transferred to a peripheral device using the communication module, and may then be further processed determine fluid parameter data such as flow rate, fluid volume, urine flow rate, urine volume, and other such fluid parameters. In this embodiment, that data may then be transferred from the peripheral device to a data server to log the fluid parameter data and store the data. It may then be transferred to an Electronic Medical Record (EMR) for use by healthcare professionals.

Figure 15:
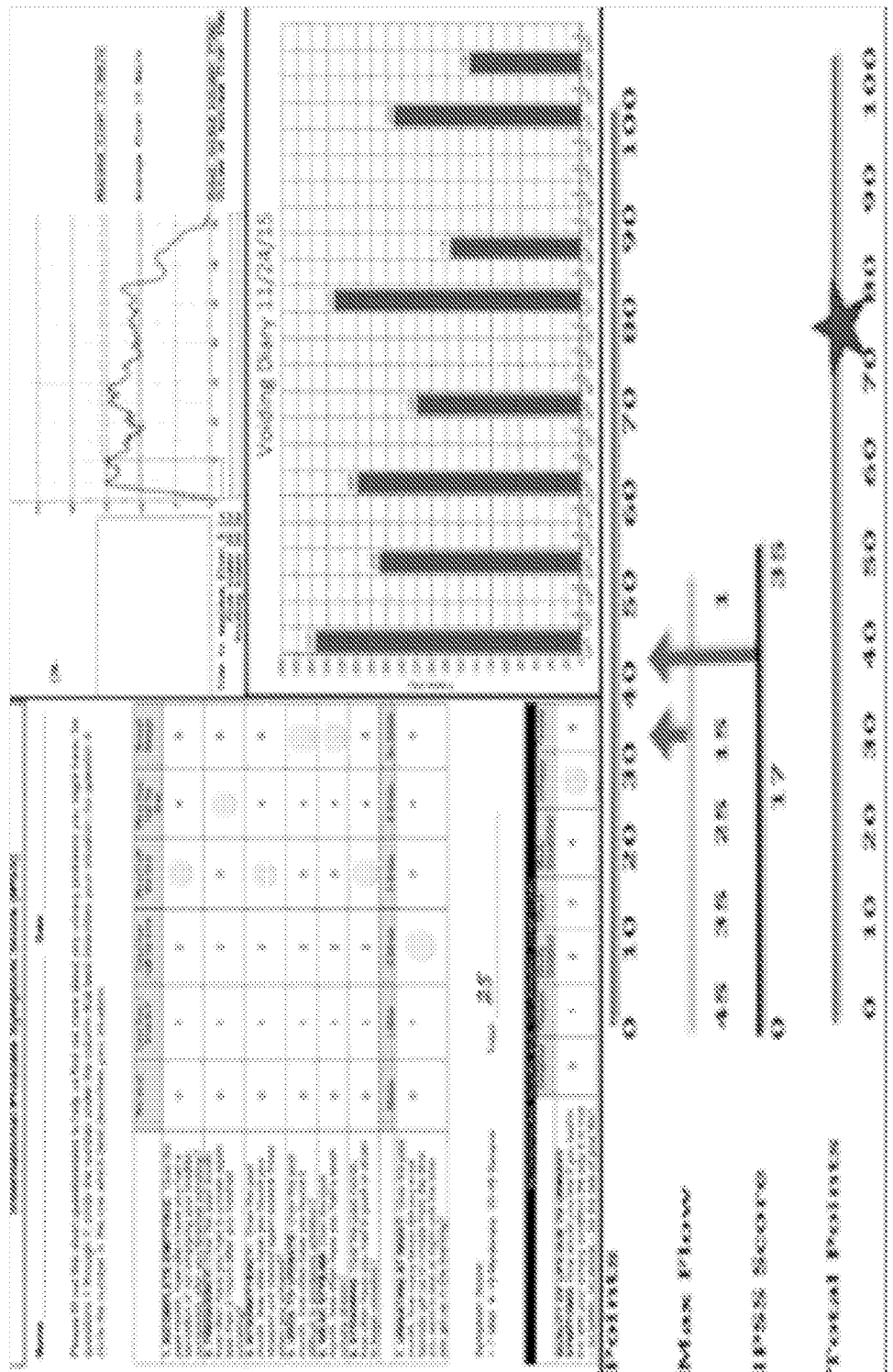
FIG. 15 is an exemplary embodiment of a physician interface for viewing data collected by the device.

In addition to measuring fluid flow characteristics and other fluid properties, the methods described above can be used to monitor the occurrence of a biological condition that is accompanied by specific fluid and flow characteristics, a specific signal that is induced chemically or by other means which is detectable by the capacitive elements and/or by additional sensors used in connection with the capacitive elements. Upon detection of this signal, the communication module can be activated and transmit the sensor data to a user, such as the individual using the fluid flow measuring device, a medical professional, or other designated person. Furthermore, the data from this device can be integrated directly into a patient's Electronic Medical Record (EMR) for easy viewing by medical specialists. A report in the form of FIG. 15 or other similar reports would facilitate a quick and comprehensive evaluation leading to a more accurate diagnosis of the patient's condition.

This device is configured to gather the fluid flow data along with other possible fluid properties, and may be used to identify anomalous health conditions and/or facilitate the basis for trending health conditions and/or artificial intelligence to assist in the early detection and/or treatment of pending negative and/or detrimental health conditions.

Various features and advantages of the invention are set forth in the following claims.

What is claimed is:

1. A fluid analysis device, comprising:
   a fluid receipt chamber having a first mechanical engagement feature and configured to receive fluid;
   a first capacitive element for measuring fluid flow of the fluid into the fluid receipt chamber; and
   a housing having a second mechanical engagement feature configured to engage with the first mechanical engagement feature of the fluid receipt chamber, the housing configured to directly contact the fluid receipt chamber when the first mechanical engagement feature and the second mechanical engagement feature are engaged, the housing including:
   a controller electrically coupled to the first capacitive element when the first mechanical engagement feature and the second mechanical engagement feature are engaged, wherein the controller is configured to:
      take a first measurement of a first capacitance of the first capacitive element based on signals received from the first capacitive element, wherein the first measurement of the first capacitance is indicative of a first volume of the fluid at a first point in time; and
      take a second measurement of the first capacitance of the first capacitive element based on signals received from the first capacitive element after waiting a sampling time, wherein the second measurement of the first capacitance is indicative of a second volume of the fluid at a second point in time, wherein a flow rate of the fluid is determinable by (1) subtracting the first volume from the second volume to determine a difference in volume and (2) dividing the difference in volume by the sampling time.

2. The fluid analysis device of claim 1, wherein the first capacitive element comprises a pair of plates, each plate having a surface, wherein the surfaces of the plates are facing one another with a first gap therebetween, wherein the first capacitance is measured across the first gap.

3. The fluid analysis device of claim 2, wherein the fluid receipt chamber comprises a double-walled chamber having an inner wall and an outer wall, wherein one of the pair of first capacitive element plates is associated with the inner wall and the other of the pair of first capacitive element plates is associated with the outer wall.

4. The fluid analysis device of claim 3, wherein the inner wall defines an inner fluid compartment, wherein the outer wall surrounds the inner wall with a fluid space therebetween, and wherein the inner fluid compartment and fluid space are fluidly connected to one another by at least one fluid passage.

5. The fluid analysis device of claim 4, wherein fluid movement between the inner fluid compartment and the fluid space is dampened by the fluid space.

6. The fluid analysis device of claim 4, further comprising a second capacitive element for measuring a second capacitance, the second capacitive element being disposed within the fluid receipt chamber such that, upon entry of fluid into the fluid receipt chamber, the second capacitive element is completely covered by fluid before the first capacitive element is completely covered by fluid.

7. The fluid analysis device of claim 6, wherein the second capacitive element comprises a pair of plates disposed within a recess, each plate having a surface wherein the surfaces of the plates are facing one another with a second gap therebetween, wherein the second capacitance is measured across the second gap.

8. The fluid analysis device of claim 7, wherein the outer wall defines an outer cup having a bottom surface, wherein the recess containing the second capacitive element is disposed below the bottom surface of the outer cup.

9. The fluid analysis device of claim 6, wherein the controller is operatively coupled to the second capacitive element, the controller configured to measure a second capacitance of the second capacitive element.

10. The fluid analysis device of claim 6, wherein one or more of the surfaces of the plates of the first capacitive element and the second capacitive element have an insulating coating applied thereto.

11. The fluid analysis device of claim 6, wherein the fluid receipt chamber is substantially cylindrical.

12. The fluid analysis device of claim 6, wherein the first capacitive element comprises a plurality of pairs of plates, each of the plurality of pairs of plates disposed symmetrically about the cylindrical fluid receipt chamber.

13. The fluid analysis device of claim 12, wherein the controller is configured to determine a plurality of first capacitances from each of the plurality of pairs of plates.

14. The fluid analysis device of claim 13, wherein the housing further includes:
a communication module, wherein the controller is operatively coupled to the communication module.

15. The fluid analysis device of claim 14, wherein the housing further comprises a tilt sensor operatively coupled to the controller to obtain tilt angle data.

16. The fluid analysis device of claim 15, further comprising a sensor component disposed within the fluid receipt chamber, the sensor component comprising a reagent strip and a sensor for reading the reagent strip.

17. The fluid analysis device of claim 16, wherein the reagent strip includes at least one portion for sensing an analyte selected from the group consisting of specific gravity (density), glucose, blood (hemoglobin), presence of proteins, leukocytes, urobilinogen, bilirubin, acidity/alkalinity (pH), presence of nitrates, sodium chloride, ketones, and beta-hCG.

18. The fluid analysis device of claim 14, wherein the controller is configured to wirelessly communicate with an external device using the communication module.

19. The fluid analysis device of claim 18, wherein the controller wirelessly communicates at least one of the first capacitance, a second capacitance, and tilt angle data to the external device.

20. The fluid analysis device of claim 1, wherein at least one of the first mechanical engagement feature and the second mechanical engagement feature includes at least one of a press fitting, a threaded engagement, a slide-on feature, or a snap-on feature.

21. The fluid analysis device of claim 1, wherein the housing is electrically coupled to the first capacitive element when the first mechanical engagement feature and the second mechanical engagement feature are engaged.

22. The fluid analysis device of claim 1, wherein the fluid receipt chamber includes:
at least one wall; and
at least one bottom surface.

23. The fluid analysis device of claim 1, wherein the fluid receipt chamber includes:
at least one wall.

24. The fluid analysis device of claim 1, wherein the fluid receipt chamber includes:
at least one bottom surface.

25. The fluid analysis device of claim 1, wherein the housing is at least one of a base or a handle.

26. A fluid analysis system comprising:
a fluid analysis device; and
an external device;
wherein the fluid analysis device includes:
a fluid receipt chamber having a first mechanical engagement feature and configured to receive fluid;
a first capacitive element for measuring fluid flow of the fluid into the fluid receipt chamber; and
a housing having a second mechanical engagement feature configured to engage with the first mechanical engagement feature of the fluid receipt chamber, the housing configured to directly contact the fluid receipt chamber when the first mechanical engagement feature and the second mechanical engagement feature are engaged, the housing including:
a controller electrically coupled to the first capacitive element when the first mechanical engagement feature and the second mechanical engagement feature are engaged, wherein the controller is configured to:
take a first measurement of a first capacitance of the first capacitive element based on signals received from the first capacitive element, wherein the first measurement of the first capacitance is indicative of a first volume of the fluid at a first point in time; and
take a second measurement of the first capacitance of the first capacitive element based on signals received from the first capacitive element based on signals received from the first capacitive element after waiting a sampling time, wherein the second measurement of the first capacitance is indicative of a second volume of the fluid at a second point in time, wherein a flow rate of the fluid is determinable by (1) subtracting the first volume from the second volume to determine a difference in volume and (2) dividing the difference in volume by the sampling time.

27. The fluid analysis system of claim 26, wherein the external device is a smart phone or a tablet computer.

28. The fluid analysis device of claim 26, wherein the external device determines a fluid parameter of the fluid in the fluid receipt chamber based on at least one of the first capacitance, the second capacitance, and the tilt angle data.

29. The fluid analysis system of claim 28, wherein the fluid parameter is selected from the group consisting of a total volume, a continuous flow rate, a flow duration time, a maximum flow rate, and an average flow rate.

30. The fluid analysis system of claim 28, wherein the second capacitance is an indication of a dielectric of the fluid in the fluid receipt chamber, and wherein the second capacitance is used to convert the first capacitance to the fluid parameter.

31. The fluid analysis system of claim 30, wherein the second capacitance is used to select at least one of a calibration curve or a lookup table to convert the first capacitance to the fluid parameter.

32. The fluid analysis system of claim 28, wherein the tilt angle data is used to select at least one of a calibration curve or a lookup table to convert the first capacitance to the fluid parameter.

33. The fluid analysis system of claim 28, wherein the first capacitance comprises a plurality of first capacitances and wherein the external device determines a tilt angle of the fluid receipt chamber based on the plurality of first capacitances.

34. The fluid analysis system of claim 28, wherein the tilt angle determined from the plurality of first capacitances is used to select at least one of a calibration curve or a lookup table to convert the plurality of first capacitances to the fluid parameter.

35. The fluid analysis system of claim 28, further comprising a data server in communication with the external device, wherein the external device transmits the fluid parameter to the data server.

36. The fluid analysis system of claim 35, wherein the fluid parameter data is converted to an electronic medical record format.

37. The fluid analysis system of claim 28, wherein the fluid comprises urine and wherein the fluid parameters comprise uroflowmetry data.

38. The fluid analysis system of claim 26, wherein at least one of the first mechanical engagement feature and the second mechanical engagement feature includes at least one of a press fitting, a threaded engagement, a slide-on feature, or a snap-on feature.

39. The fluid analysis system of claim 26, wherein the housing is at least one of a base or a handle.

40. A fluid analysis device, comprising:
- a fluid receipt chamber having a first mechanical engagement feature and configured to receive fluid;
- a first capacitive element for measuring fluid flow of the fluid into the fluid receipt chamber; and
- a base having a second mechanical engagement feature configured to engage with the first mechanical engagement feature of the fluid receipt chamber, the base configured to directly contact the fluid receipt chamber when the first mechanical engagement feature and the second mechanical engagement feature are engaged, the base including:
- a controller electrically coupled to the first capacitive element when the first mechanical engagement feature and the second mechanical engagement feature are engaged, wherein the controller is configured to:
  - take a first measurement of a first capacitance of the first capacitive element based on signals received from the first capacitive element, wherein the first measurement of the first capacitance is indicative of a first volume of the fluid at a first point in time; and
  - take a second measurement of the first capacitance of the first capacitive element based on signals received from the first capacitive element after waiting a sampling time, wherein the second measurement of the first capacitance is indicative of a second volume of the fluid at a second point in time, wherein a flow rate of the fluid is determinable by (1) subtracting the first volume from the second volume to determine a difference in volume and (2) dividing the difference in volume by the sampling time.

* * * * *